US007049594B2

(12) United States Patent
Wu et al.

(10) Patent No.: US 7,049,594 B2
(45) Date of Patent: May 23, 2006

(54) POSITION SENSING SENSOR, METHOD AND SYSTEM

(75) Inventors: Chunwu Wu, Portage, MI (US); Waldean A. Schulz, Boulder, CO (US)

(73) Assignee: Howmedica Leibinger, Kalamazoo, MI (US)

( * ) Notice: Subject to any disclaimer, the term of this patent is extended or adjusted under 35 U.S.C. 154(b) by 348 days.

(21) Appl. No.: 10/402,586

(22) Filed: Mar. 28, 2003

(65) Prior Publication Data
US 2004/0188616 A1    Sep. 30, 2004

(51) Int. Cl.
*G01J 5/08*    (2006.01)
(52) U.S. Cl. .............................. 250/338.1; 250/363.06; 250/559.29; 363/141.2
(58) Field of Classification Search ............. 250/338.1, 250/363.06, 559.29; 356/141.2
See application file for complete search history.

(56) References Cited

U.S. PATENT DOCUMENTS

| 4,595,014 A | 6/1986 | Barrett et al. ............... 128/654 |
| 5,036,546 A | 7/1991 | Gottesman et al. ........... 382/65 |
| 5,099,128 A | 3/1992 | Stettner et al. ......... 250/370.11 |
| 5,196,900 A | 3/1993 | Pettersen .................... 356/141 |
| 5,499,098 A | 3/1996 | Ogawa ....................... 356/375 |
| 5,502,568 A | 3/1996 | Ogawa et al. .............. 356/375 |
| 5,640,241 A | 6/1997 | Ogawa ....................... 356/375 |
| 5,757,478 A | 5/1998 | Ma .......................... 356/141.2 |
| 5,764,810 A | 6/1998 | Xie ............................ 382/252 |
| 5,792,147 A | 8/1998 | Evans et al. ................ 606/130 |
| 6,141,104 A | 10/2000 | Schulz et al. .............. 356/375 |
| 6,180,946 B1 | 1/2001 | Ebstein ................... 250/370.11 |
| 6,392,235 B1 | 5/2002 | Barrett et al. .......... 250/363.06 |
| 2002/0075990 A1 | 6/2002 | Lanza et al. |

OTHER PUBLICATIONS

Int'l Search Report and Written Opinion Appl. No. PCT/US04/09466 and dated Jan. 13, 2005.

*Primary Examiner*—Otilia Gabor
*Assistant Examiner*—Christine Sung
(74) *Attorney, Agent, or Firm*—McCracken & Frank LLP

(57) ABSTRACT

A sensor for determining a component of a location of a radiation source within a three dimensional volume includes a mask having a series of openings that has a predetermined mathematical relationship among the openings within the series of openings and defines a mask reference line; a detector surface spaced from the mask where radiation passing through the mask creates a mask image on the detector surface having a series of peaks and an image reference line within the mask image that can be located and where at least 50% of the mask image is projected onto the detection surface; and a calculating unit to determine a location of the image reference line within the mask image and the component of the location of the radiation source from the calculated location of the image reference line within the mask image. A method and system for using this sensor are also disclosed.

66 Claims, 23 Drawing Sheets

POSITION SENSING SENSOR, METHOD AND SYSTEM

FIELD OF THE INVENTION

This invention relates to an angle sensing sensor, a position determining system, and a method for determining a component of the location of a radiation source. More particularly, this invention relates to a position sensing sensor and a method and system for determining the location of a component of a radiation source within a predefined volume.

BACKGROUND OF THE INVENTION

In recent years, there has been increased use by surgeons of computer assisted surgical navigation devices to assist them in determining the location of their surgical instruments relative to a patient's anatomy. Many of these surgical navigation systems and devices utilize small "point sources" of light and sensors for these light sources to determine the spatial position of a surgical tool relative to a patient's anatomy. The light sources historically have been light emitting diodes (LED's). A typical surgical tool includes multiple LED's positioned such that these LED's do not lie in a single plane. The determination of the location of these LED's for a properly calibrated tool can determine both the position of that tool and also the orientation of that tool within a three dimensional surgical space or volume.

Typical surgical navigation systems utilize multiple separately spaced apart detectors and associated computer software to determine the position of each of the LED's on a surgical device or instrument. In these systems, the light sources are small relative to the distance and volume and therefore are considered to be point sources of light. Typical LED's emit infrared light; however, light of other wavelengths, including light in the visible spectrum, can be used. These systems determine the relative angle of each light source entering an individual detector and the system combines the angle from each detector to calculate the three dimensional x, y, z coordinates for a particular light source. From the position of the LED's on a surgical instrument, the system can calculate the exact location of a properly calibrated instrument.

Typical detectors for these light or radiation sources may be position sensitive detectors (PSD), linear photo diode arrays or linear charged coupled devices (CCD). In the case of the CCD, these typical systems include a CCD array that is one pixel wide and a thousand or more pixels long, so that a significant volume can be detected. Typically the light from the point source passes through a lens or narrow slit so as to focus a thin line of light onto the CCD that in turn will illuminate a small number of contiguous pixels. Depending upon the size of the pixels in the CCD and the ability of the system to focus the light, the position of the light on that detector is typically assumed to be either the center point of the pixels that have been illuminated or the pixel with the highest light intensity.

As surgical navigation and other position detection systems become more accurate, the accuracy of the lens or the slit that focuses the light from the point source onto the position sensing device becomes a limiting factor for system accuracy.

SUMMARY OF THE INVENTION

The present invention is a method of determining a component of a location of a radiation source within a three dimensional volume. This method includes the steps of passing radiation from the radiation source through a mask that has a series of openings onto a detector surface. The series of openings has a predetermined mathematical relationship among the openings within the series of openings and the series of openings define a mask reference line. A mask image having a series of peaks and an image reference line is created such that the image reference line within the mask image that can be located. At least 50% of the mask image is projected onto the detector surface. The location of the mask image on the detector is calculated. Next, the location of the image reference line within the mask image is calculated and lastly the component of the location of the radiation source is calculated from the calculated location of the image reference line within the mask image.

A further aspect of the present invention relates to a system to determine a component of the location of a radiation source within a three dimensional volume that includes a mask having a series of openings wherein the series of openings has a predetermined mathematical relationship among the openings within the series of openings and wherein the series of openings define a mask reference line. The system also includes a detector surface spaced from the mask wherein the mask creates a mask image on the detector surface having a series of peaks and having an image reference line within the mask image that can be located. At least 50% of the mask image is projected onto the detector surface. The system further includes a first circuit to calculate a location of the image reference line within the mask image and a second circuit to calculate the component of the location of the radiation source from the calculated location of the image reference line within the mask image.

A still further aspect of the present invention is directed to a sensor to determine a component of a location of a radiation source within a three dimensional volume. This sensor comprises a mask having a series of openings wherein the series of openings has a predetermined mathematical relationship among the openings within the series of openings and wherein the series of openings define a mask reference line, a detector surface spaced from the mask where the mask creates a mask image on the detector surface having a series of peaks and having an image reference line within the mask image that can be located. At least 50% of the mask image is projected onto the detector surface. The sensor also includes a calculating unit to determine a location of the image reference line within the mask image and the component of the location of the radiation source from the calculated location of the image reference line within the mask image.

Other aspects and advantages of the present invention will become apparent upon consideration of the following detailed description.

DETAILED DESCRIPTION OF THE PREFERRED EMBODIMENTS

Figure 1:
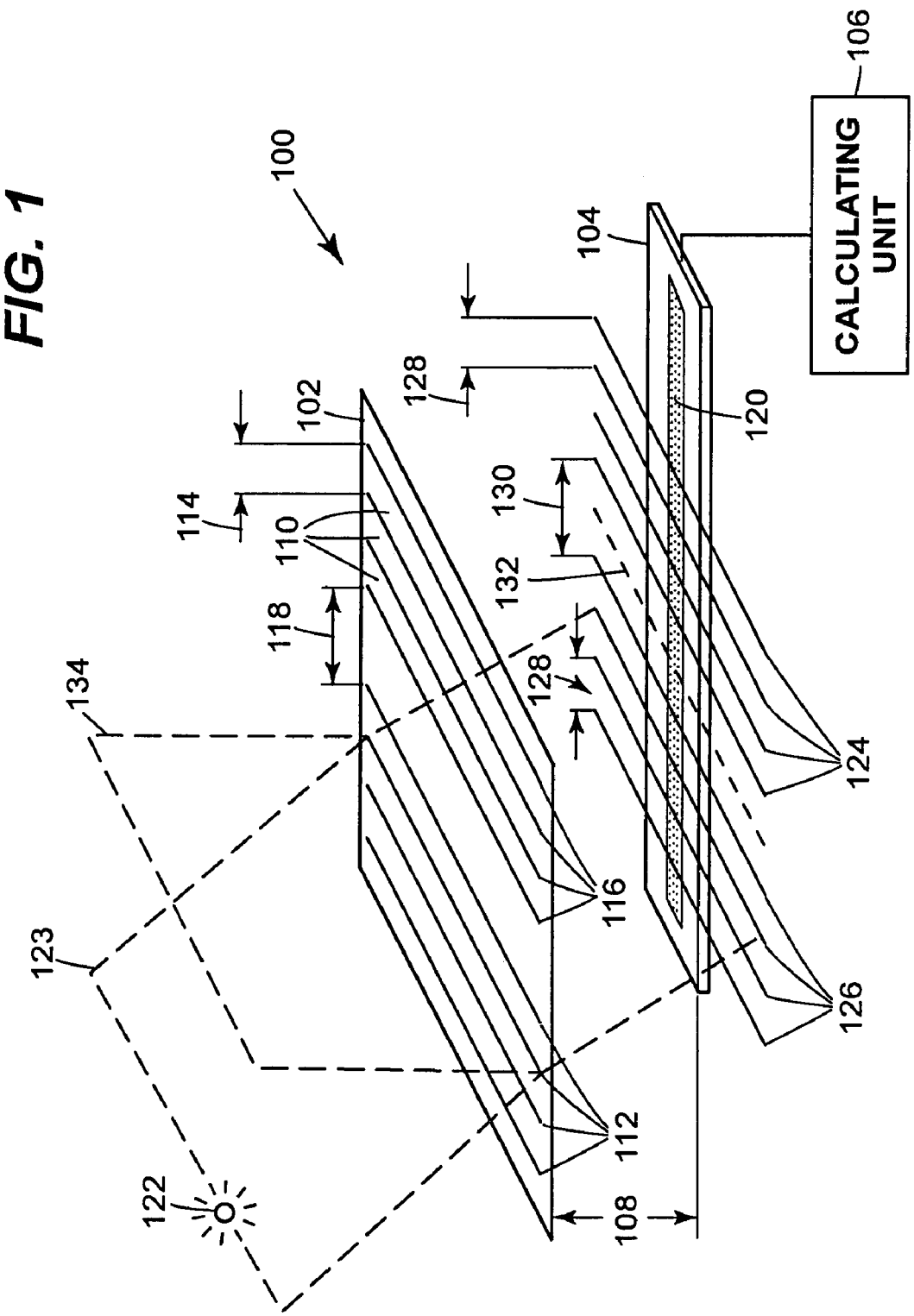
FIG. 1 is an orthographic representation of the sensor of the present invention.

FIG. 1 is an orthographic view of a sensor 100 for use in the system and method of the present invention. The sensor 100 includes a mask 102, an image detector 104 and a calculating unit 106. The mask 102 is spaced from the image detector 104 by a distance 108. The mask 102 has two series of slits 110 and 112. Each of the slits within the series of slits 110 and 112 is spaced a distance 114 from its neighboring slit within the same series 110 or 112. Between the series of slits 110 and 112 is a central opaque area 116, which has a spacing 118 that is larger than the spacing 114.

The image detector 104 can be any of a series of conventional image detecting devices including a CCD detector having a thousand or more pixels placed in a row that is one or more pixels wide along the length of the image detector 104. The length of the image detector 104 preferably should be longer than the width of the series of slits 110 and 112, including the central opaque area 116, if present. These pixels comprise an active detector surface 120 of the image detector 104. As noted previously, the image detector 104 can be any suitable commercial light or radiation detection device including a CCD such as Toshiba TCD1304AP, or Dalsa IL-C6-2048, or any other linear CCD. While it is possible to use other types of detection devices such as PSD devices, because of the complex nature of the images received on the image detector 104, it is preferred to use a CCD or a CMOS photodiode array having a very large number of discreet pixels in the array. A sufficient number of pixels present in the image detector 104 insures accuracy of the determination of a location of a light source. As noted above, the image detector 104 is spaced from the mask 102 by the distance of 108. The choice of the distance 108 and the size of the slits in the series of slits 110 and 112 should be made to minimize the diffraction of the radiation passing through the mask 102 and received on the image detector 104. The specific values for the size and number of the slits within the series of slits 110 and 112 and the distance 108 as well as the spacing 114 and 118 can be determined by techniques well known to those skilled in the art and will be discussed in more detail with regard to specific embodiments hereinafter.

A radiation source 122, such as an infrared LED, located within a predetermined volume to be detected by the detector 100 emits radiation in an infinite series of planes including a plane 123 that passes through one of the slits in the series of slits 112. Radiation from different planes (not shown) will pass through the other slits in the series of slits 112 and the slits in the series of slits 110. As the radiation from the radiation source 122 passes through the slits in the series of slits 110 and 112 it forms a mask image on the image detector 104 that comprises a series of images 124 and 126 corresponding to the slits in the series of slits 110 and 112. Because the image detector 104 is spaced the distance 108 away from the mask 102, a spacing 128 between the respective series of images 124 and 126 will be slightly different than the spacing 114 of the slits in the series of slits 110 and 112. Similarly, a shadow 130 will have a different size than the width 118 of the central opaque area 116. As shown in FIG. 1 as a dotted line, an image reference line 132 is equidistant from the edges of the shadow 130. The plane 123 on which the radiation from the radiation source 122 travels is at angle θ with respect to a plane 134, which is perpendicular to the image detector 104. At least 50% of the mask image should be projected onto the image detector 104.

As will be discussed more fully hereinafter, the location of each of the individual images that constitute the mask image within the series of images 124 and 126 is determined and from the position of each of the images within the series of images 124 and 126, the exact location of the image reference line 132 can be determined. The calculating unit 106 calculates the position of the image reference line 132 from the position of each of the images within the series of images 124 and 126 and this position data is sent to a computer as more fully discussed with reference to FIG. 19.

Also as noted shown in FIG. 1, each of the slits within the series of slits 110 and 112 in the mask 102 are considerably longer than the width of the active detector surface 120. As the radiation source 122 is moved about within the predetermined three-dimensional volume the length of each of the slits within the series of slits 110 and 112 ensures that some portion of the series of images 124 and 126 will illuminate the active detector surface 120. This insures that the size of the field of view is not unnecessarily restricted by slits that simply are not long enough.

Figure 2:
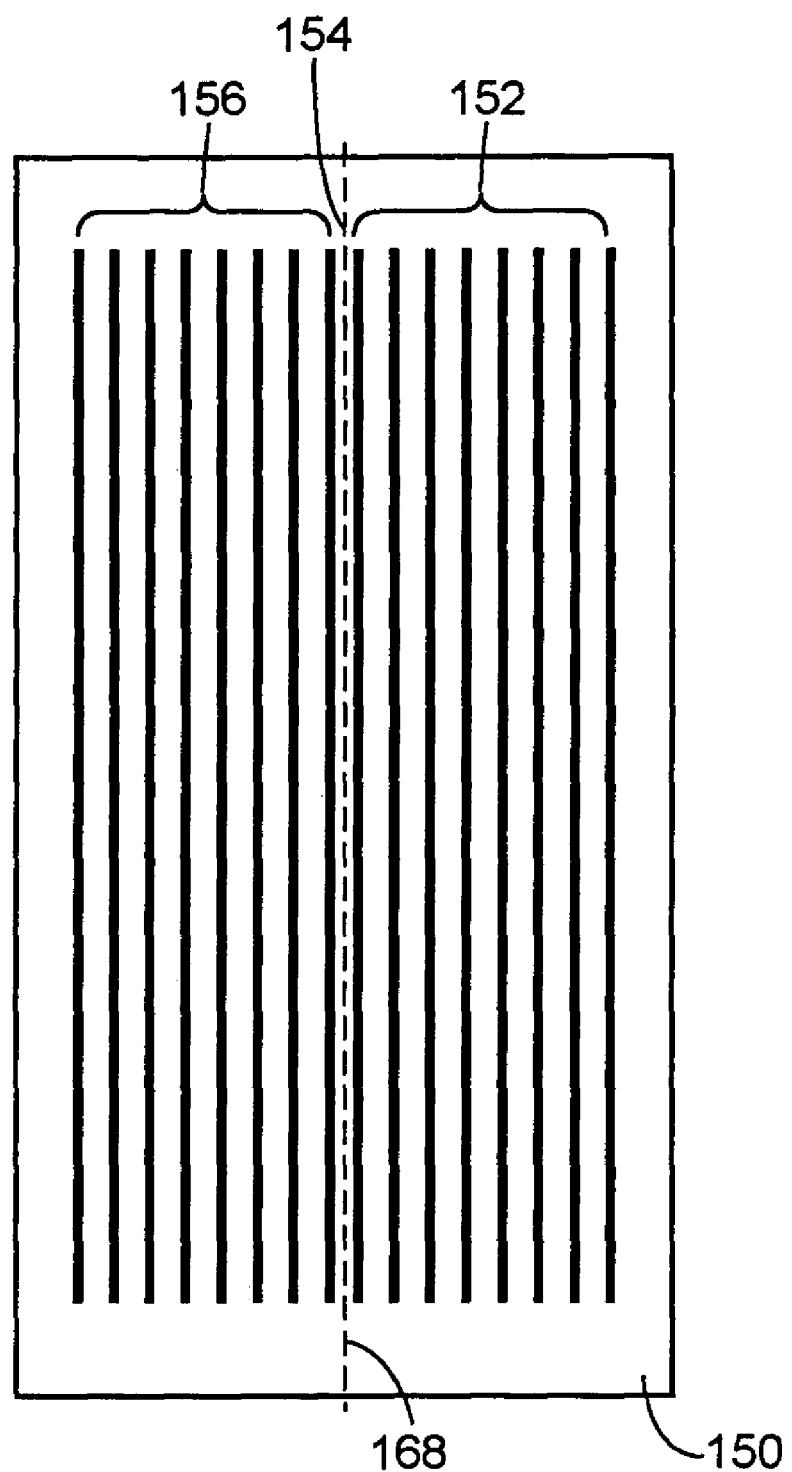
FIG. 2 is a plan view of a mask showing one slit pattern design.
Figure 3:
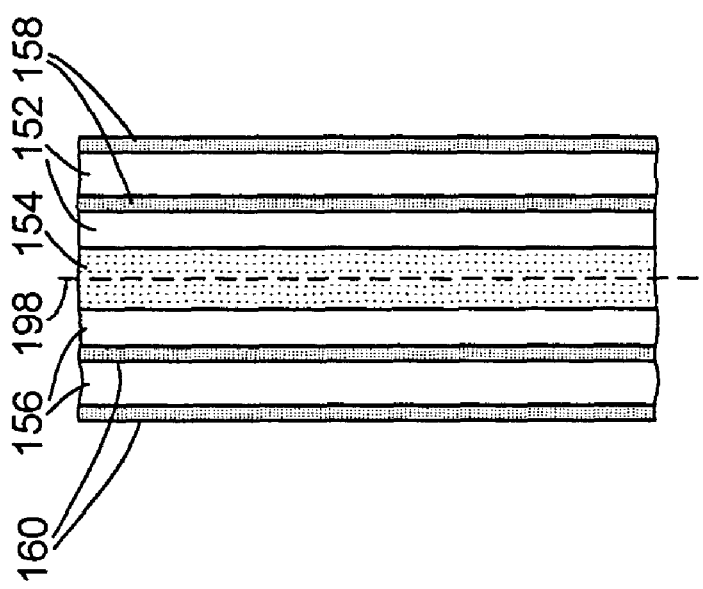
FIG. 3 is a partial plan view showing the spacing of the central slits of the mask of FIG. 2.

Referring now to FIG. 2, which shows a plan view of a mask slit pattern that has been schematically shown in FIG. 1. A mask 150 has a series of slits 152 to the right of a central opaque area 154. There are 15 slits in the series of slits 152. There are also 15 slits in a similar series of slits 156 to the left side of the central opaque area 154. Each slit in the series of slits 152 and 156 is about 0.2 millimeters wide and longer than the length of the image detector 104. In one embodiment, the series of slits 152 and 156 are about 35 millimeters long. Each adjacent slit in series of slits 152 and 156 is separated from its neighboring slit within the same series by a distance of 0.2 millimeters. In the embodiment shown in FIG. 2, the central opaque area 154 is about 0.4 millimeters wide. FIG. 3 shows an enlarged partial plan view of the center portion of the mask 150. It shows opaque areas 158 and 160 that are about 0.2 millimeters between each of the slits in the series of slits 152 and 156. In one embodiment, the mask 150 is placed about 29 mm above the image detector 104. A mask reference line 168 is shown passing through the center of the central opaque area 154.

Figure 22:
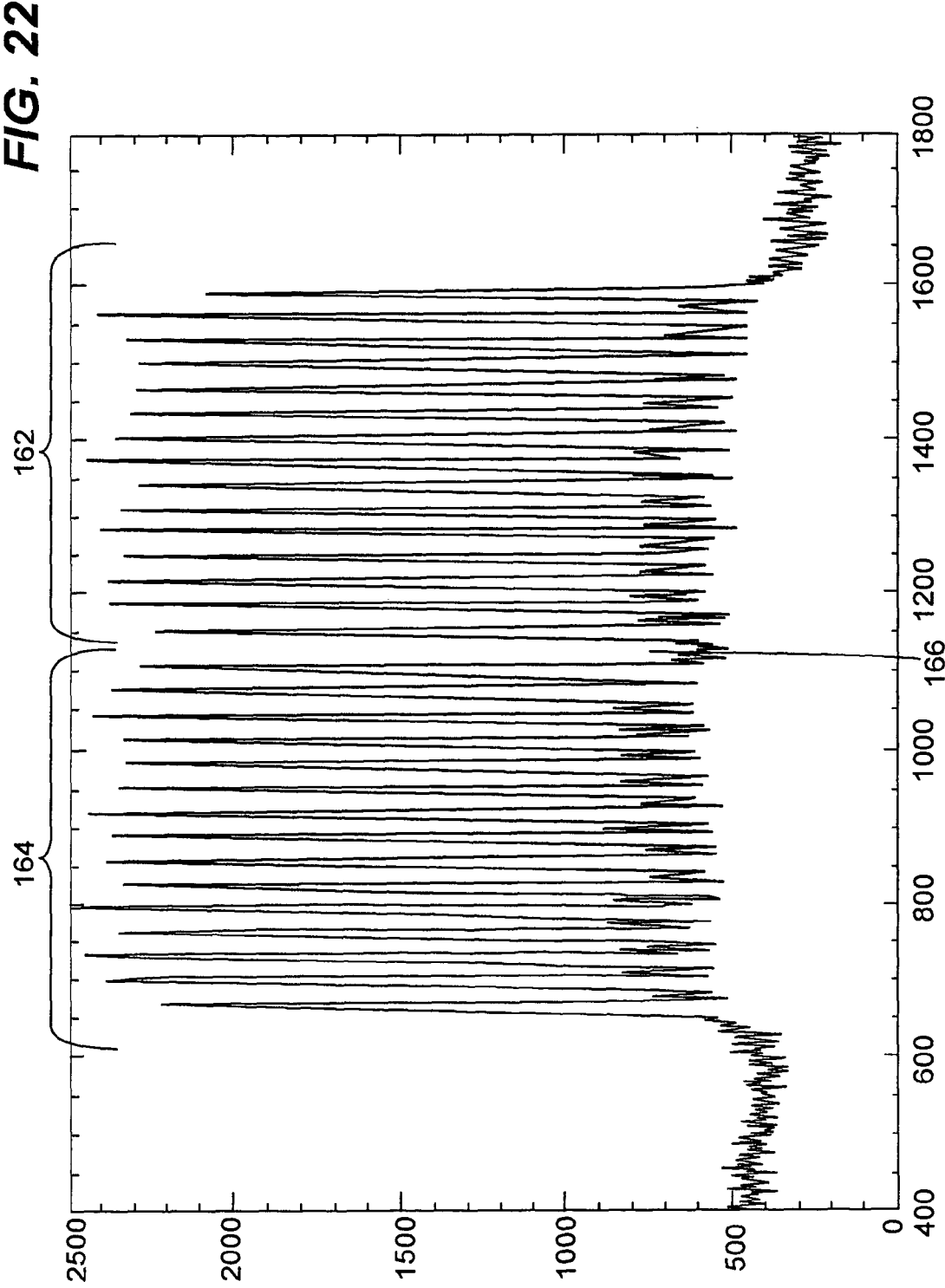
FIG. 22 is a plot of the intensity on the detector of the light passing through the mask of FIG. 2.
Figure 23:
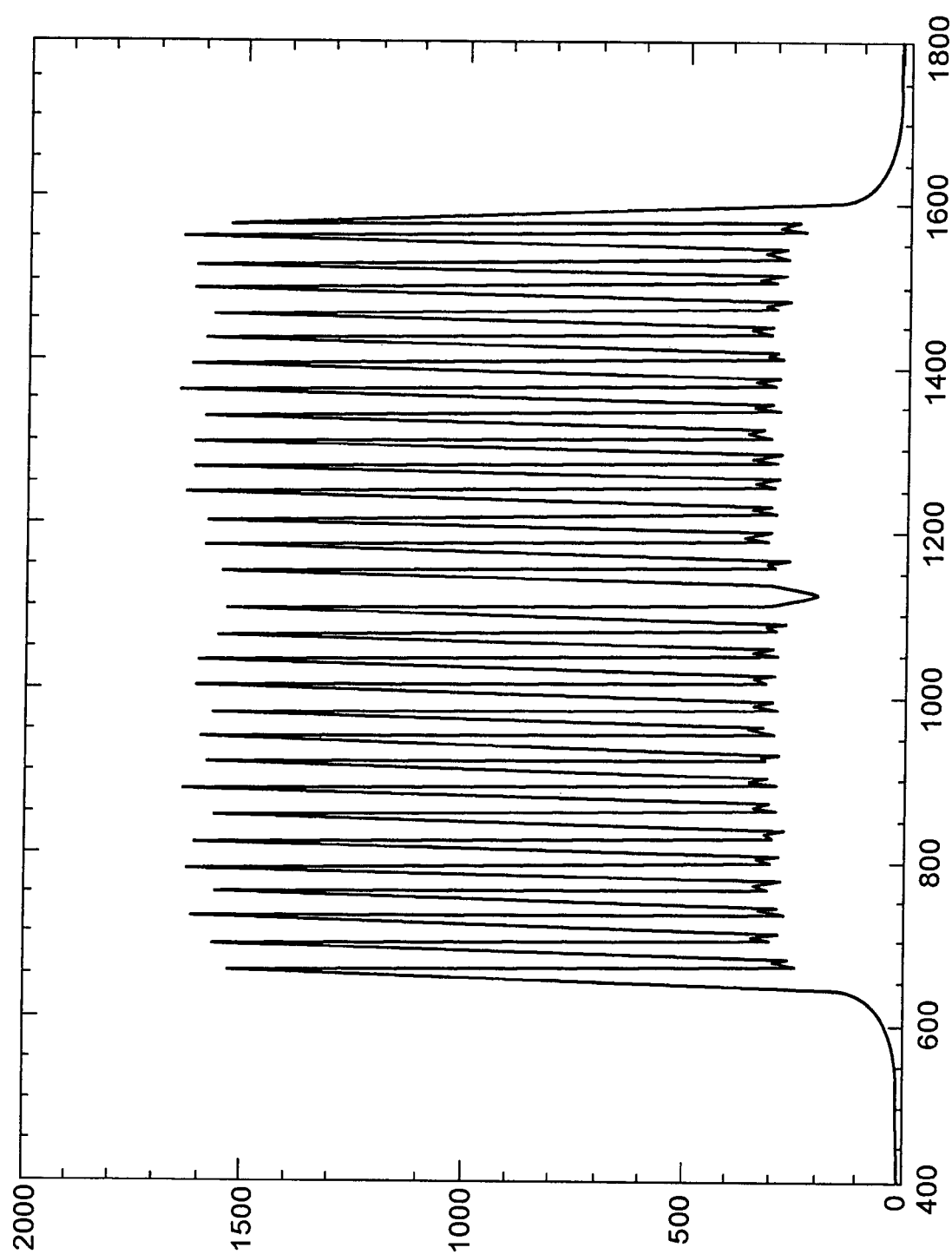
FIG. 23 is a plot of the intensity data of FIG. 22 that has been filtered to remove background light.

Light passing through the mask 150 of FIG. 2 onto the image detector 104 creates an image that has an intensity on the image detector 104 as shown in FIG. 22. The plot of the image intensity shows a series of 15 peaks 162 on the right portion of the image and a series of 15 peaks 164 on the left portion of the image. The x-axis of the graph is the position along the image detector 104, also known as the CCD pixel index, and the y-axis is the intensity of the radiation on each of the pixels of the image detector 104. The data includes a wider central valley 166 that corresponds to the central opaque area 154 of the mask 150. The data in FIG. 22 is raw data as detected by the image detector 104 and contains considerable noise from the background or ambient light that also reaches the image detector 104. If desired for ease of data manipulation, filtering and smoothing can be applied to the data shown in FIG. 22 to remove, or at least minimize the background noise and improve the signal to noise ratio. The image as shown in FIG. 23 is the data of FIG. 22 that has been smoothed by use of a boxcar filter using a known methodology. Instead of a boxcar filter, any of the numerous well-known data filtering or smoothing techniques can be used including Hanning, or Butterworth filters and the like. The peaks as shown in FIG. 23 are much more regular but there still is a bias of about 300 units of intensity caused by the diffraction of the radiation as it passes through the slits in the series of slits 152 and 156.

It may be desirable to further smooth the data shown in FIG. 23 by convolving the data with a kernel of the distance in pixels between adjacent slits within the series of slits 152 and 156. This convolving process results in a data set similar to that shown in FIG. 24. The data shown in FIG. 24 removes the bias caused by the diffraction of the radiation through the slits in the series of slits 152 and 156. Note also that the peaks in FIG. 23 become positive peaks and valleys in FIG. 23 become negative extrema. The data of FIG. 24 is preferably used to estimate the peak locations.

Figure 24:
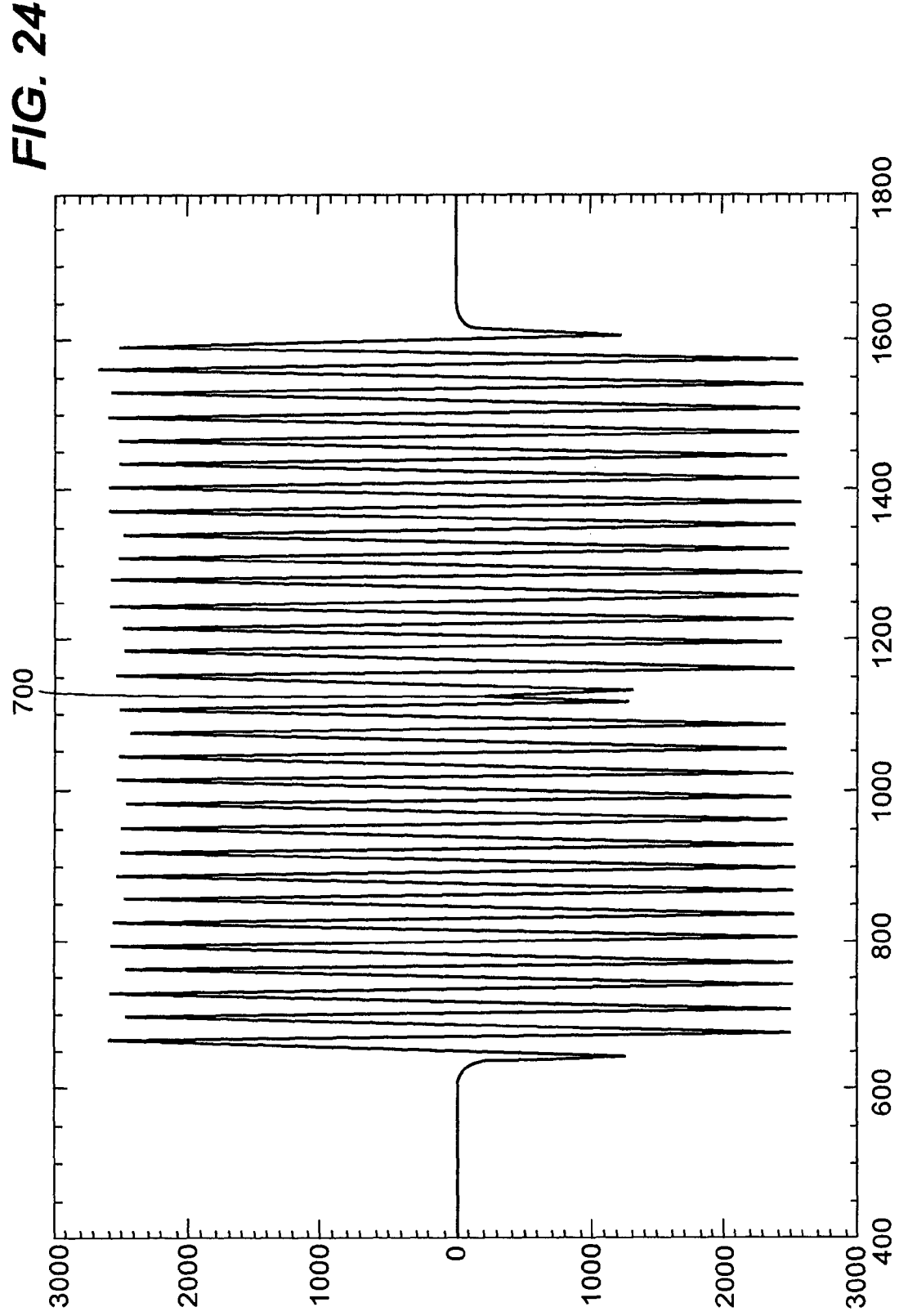
FIG. 24 is a plot of data of FIG. 23 that has been convolved with the system kernel.

As will be described later, the data as shown in FIGS. 22, 23, and 24 can be used to determine the location of the image reference line 132 corresponding to a mask reference line 168 which passes down the middle of the central opaque area 154. Once the location of the image reference line 132 corresponding to the mask reference line 168 is determined, then the location of the component of the radiation source that created the image as shown in FIG. 22 can easily be determined by methods well known to those of ordinary skill in the art.

Figure 5:
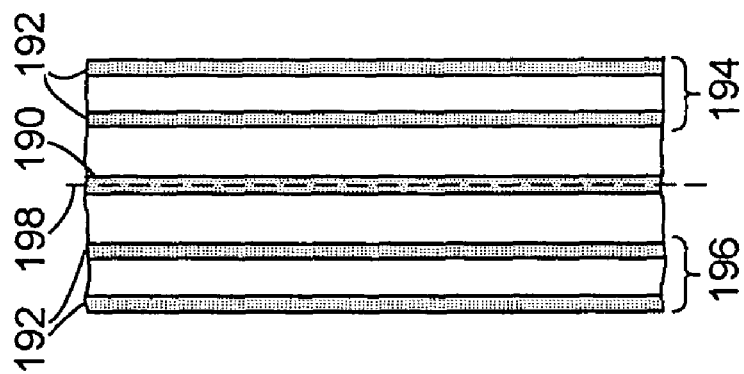
FIGS. 4–8 are views similar to FIG. 3 showing alternative mask slit pattern designs.
Figure 4:
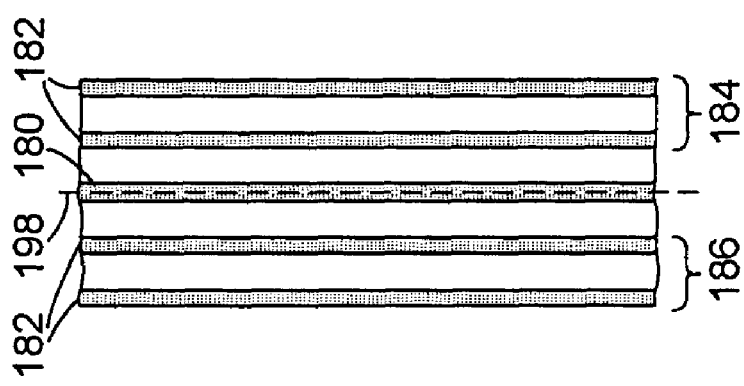

FIGS. 4 and 5 are partial views similar to FIG. 3 of alternative designs of the mask 150 as shown in FIG. 2. As shown in FIG. 4, a central opaque area 180 is the same size as an opaque area 182 between each of the series of slits 184 and 186. The primary difference between the mask of FIG. 3 and the mask of FIG. 4 is that the dimension of the central opaque area 180 in FIG. 4 is exactly the same size as the opaque area 182 between the each of the series of slits 184 and 186 whereas in the FIG. 3 the central opaque area 154 is twice the size of the opaque areas 158 and 160. Similarly, in FIG. 5 the central opaque area 190 is half the size of the opaque area 192 between the series of slits 194 and 196. In actuality, the exact design of the mask is not particularly important so long as there are sufficient number of slits in the series of slits on the mask such that the location of the image reference line 132 corresponding to a mask reference line 198 which is down the center of the central opaque areas 154, 180, and 190 in FIGS. 3, 4 and 5 and perpendicular to the length of the image detector 104 can be mathematically determined with a desired level of precision and confidence from the location of the peaks of each of the images cast on the image detector 104 by the respective mask as shown in FIGS. 3, 4, and 5. Also, while the size of the opaque areas 152, 182, and 192 are shown as being the same size for each pair of slits within each of the respective series of slits, these opaque areas can also have varying sizes within a particular series of slits, so long as the relationship among slits within the series of slits is known and can be described mathematically. In addition, there can be more than two series of slits within the mask and, as will be discussed hereinafter, the mask reference line need not be in the center of the mask. For masks that have more than two series of slits, these masks will have multiple key areas, either transparent or opaque. The size of each series of slits can vary and need not be identical to the other series of slits in the mask. So long as the mask can be defined mathematically and the mask has a mask reference line, the relative size and relation of the series of slits on a mask is not important.

Figure 6:
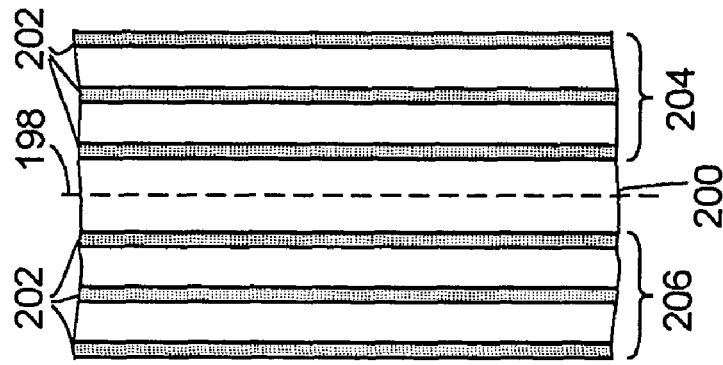
Figure 7:
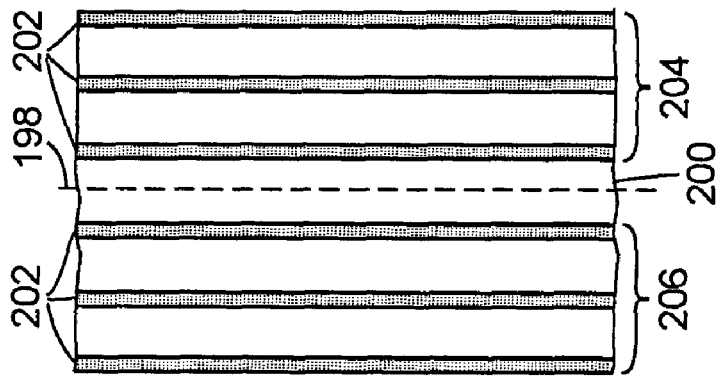
Figure 8:

Turning now to FIGS. 6, 7, and 8, the masks shown in these figures are mirror images of the masks shown in FIGS. 3, 4, and 5. In this regard, instead of having a central opaque area in FIG. 6, 7, and 8, there is an additional central slit between 200 formed by the opaque areas 202 between the respective series of slits 204 and 206. In this regard whereas the mask 150 as shown in FIG. 2 has 30 slits, 15 on each side of the central opaque area 152, the masks shown in FIGS. 6, 7, and 8 will have 31 slits, 15 on each side of the central slit 200, plus the central slit 200. Similarly, FIGS. 7 and 8 are similar to the mask of FIG. 6 except that the width to the central slit 200 is the same size as the slits 204 and 206 in FIG. 7 and in FIG. 8 the central slit 200 is smaller than the size of the series of slits 204 and 206.

As light passes through the masks shown in FIGS. 4, 5, 6, 7, and 8, the light will create images similar that shown in FIG. 22 which can then be manipulated to determine the location of the image reference line 132 which is the projection of the mask reference line 198 which passes down the center of the opaque as shown in FIGS. 3, 4, and 5 and the central slit as shown in FIGS. 6, 7, and 8. It should be appreciated that the masks can have more than two series of slits. Further, since the central slit 200 in FIG. 7 is the same size as the other slits 204 and 206 and the central opaque area 180 in FIG. 4 is the same as opaque areas 182, the mask as shown in FIGS. 4 and 7 are really both a single series of slits.

Figure 9:
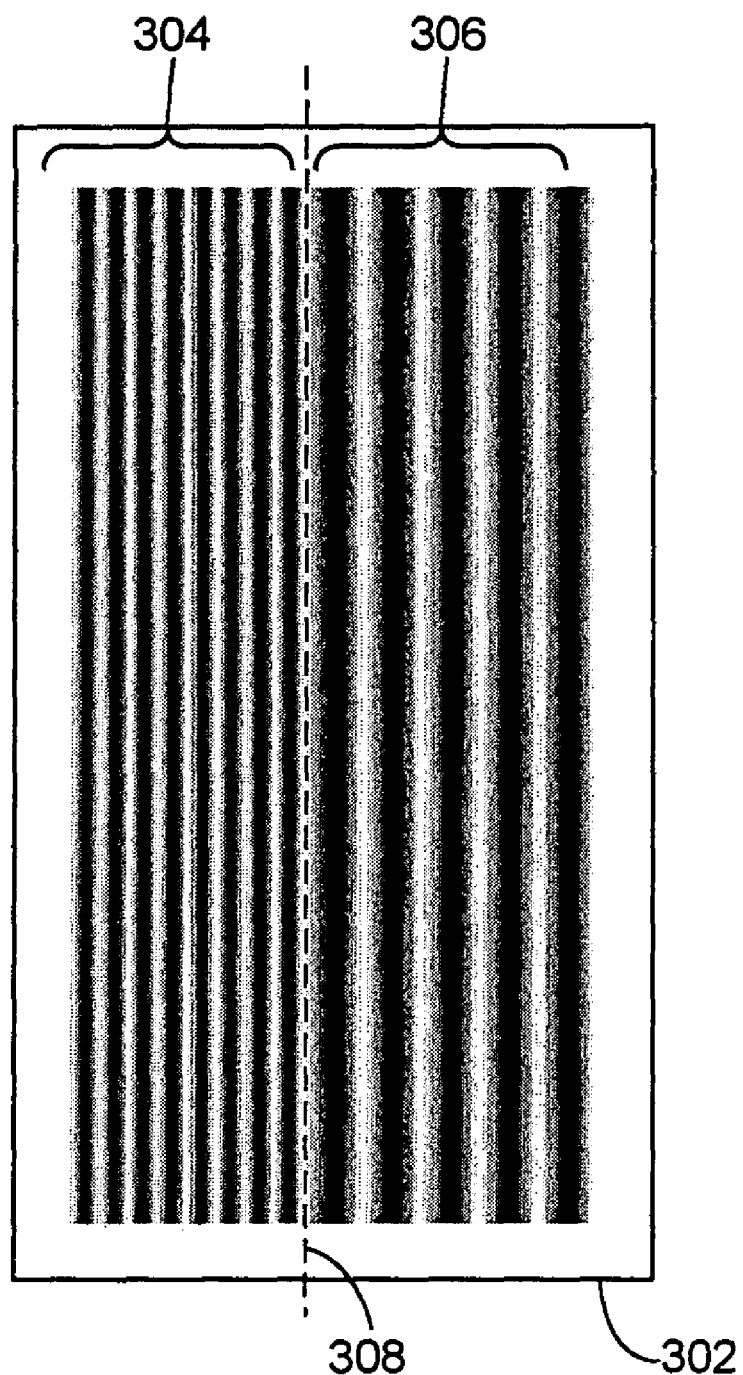
FIG. 9 is a plan view of a further alternative mask transparency design.
Figure 10:
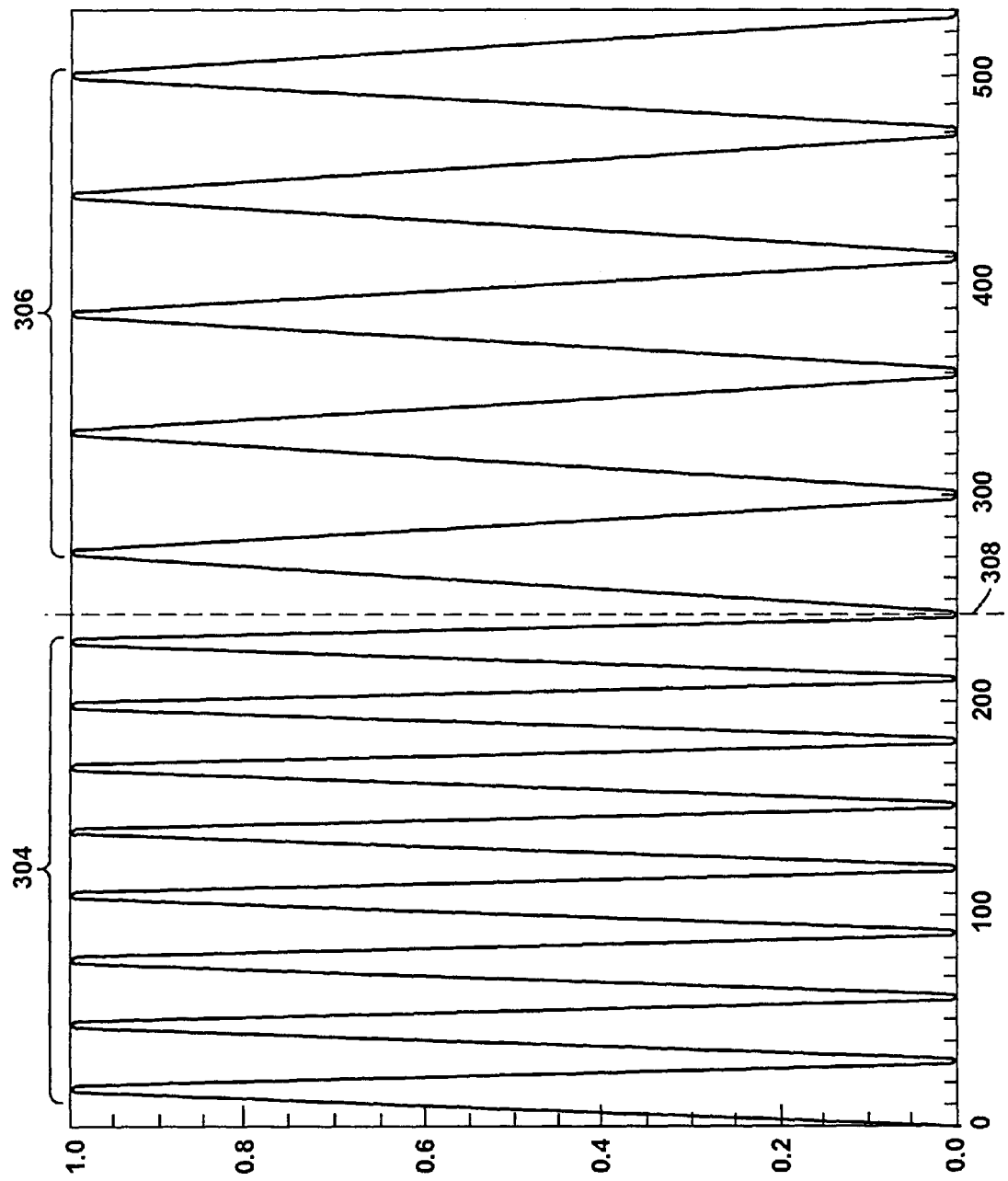
FIG. 10 is a plot of the transparency of light through the mask of FIG. 9 showing a plot of the light intensity of a light source passing through the mask.

Each of the masks shown in FIGS. 2–8 can also be represented by a mathematical function where each opaque area has a value of 0 and each slit has a value of 1. It is also possible to use other different mathematical functions to create the mask so long as the respective slits and openings in the mask have a known relation to each other. As used in this specification and the attached claims, the predetermined mathematical relationship among the openings can be either a known distance between neighboring totally opaque and totally transparent areas of a mask or a known transparency relative to the neighboring areas of the mask. For instance, as shown in FIGS. 9 and 10, a mask 302 is illustrated wherein the mask 302 has a variable transparency defined by two different sine functions 304 and 306 on either side of a mask reference line 308. The specific transparency of any section of the mask 302 will vary according to a sine function between 100% opaque and 100% transparent. The transparency of the two representative sine functions is shown in the graph of FIG. 10. It is apparent from looking at FIG. 10 on the left side of the mask reference line 308 the sine function 304 has 8 waves with a period of 30 pixels. On the right side of mask reference line 308, the sine function 306 has 5 waves with a period of 60 pixels, twice the period of the sine function 304. The mask 302 has identical transparency in the vertical direction for any location x along the length of the mask and the transparency of mask 302 at any location x along the length of the mask Knl(x) can be mathematically described by the following function:

$$Knl(x)=0.5*(1+\sin(A1*(x-knl\_offset)-\pi/2)) \text{ for } 0<=x<=knl\_offset \text{ and}$$

$$Knl(x)=0.5*(1+\sin(A2*(x-knl\_offset)-\pi/2)) \text{ for } knl\_offset<x<Nknl$$

wherein the base period (T) is 30; the number of base periods on the left of the mask reference line (Lhf) is 8; the number of base periods on the right of the mask reference line (Rhf) is 10; the size of the image kernel (Nknl) is equal to (Lhf+Rhf)*T; the offset of the mask reference line 308 from the center of the mask 302 (Knl_offset) is equal to T*Lhf; the constant for the sine function 304 (A1) is equal to $2*\pi/T$; and the constant for the sine function 306 (A2) is equal to $\pi/T$.

Figure 11:
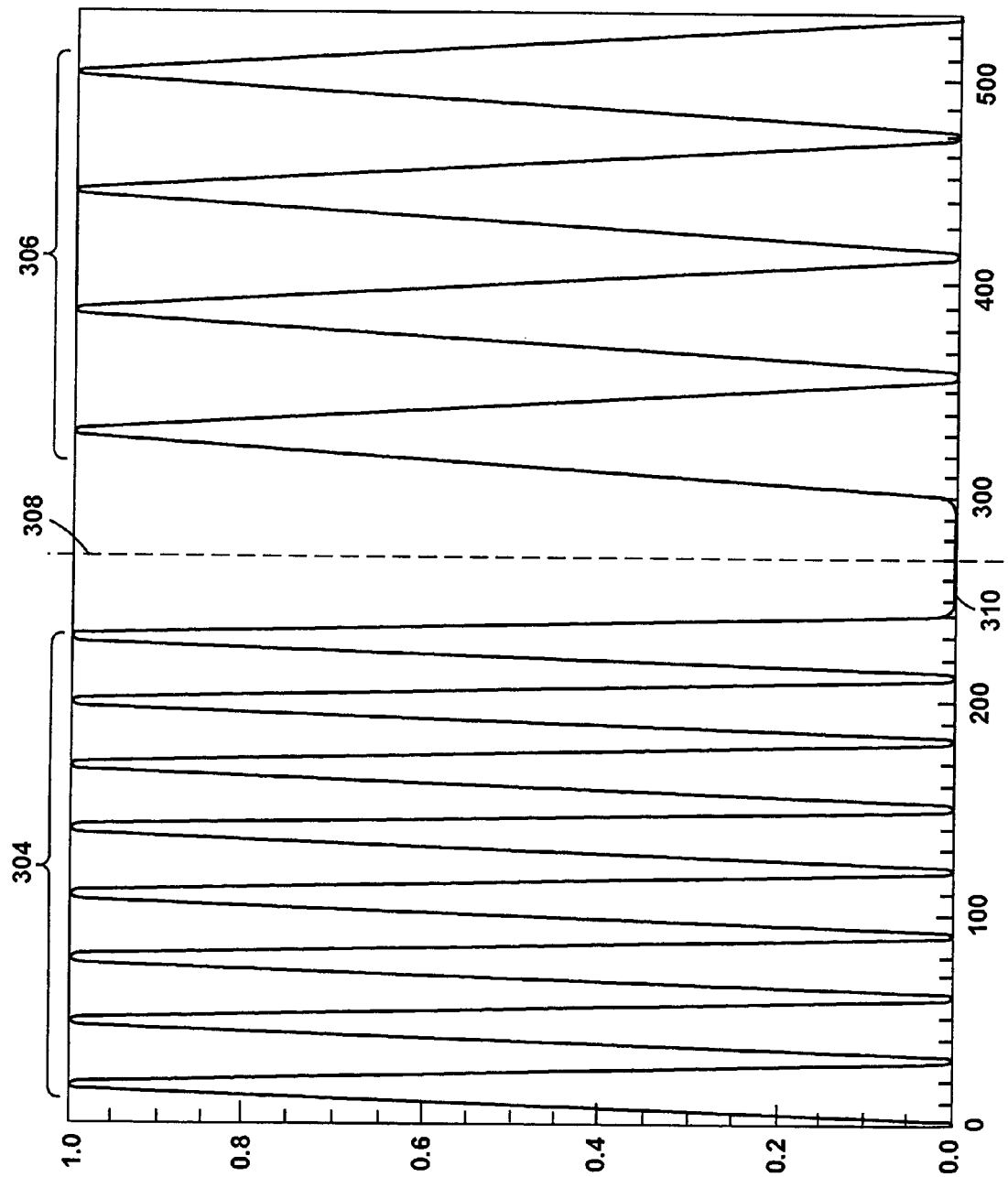
FIGS. 11–13 are plots of transparency patterns similar to FIG. 10 of alternative masks.
Figure 12:
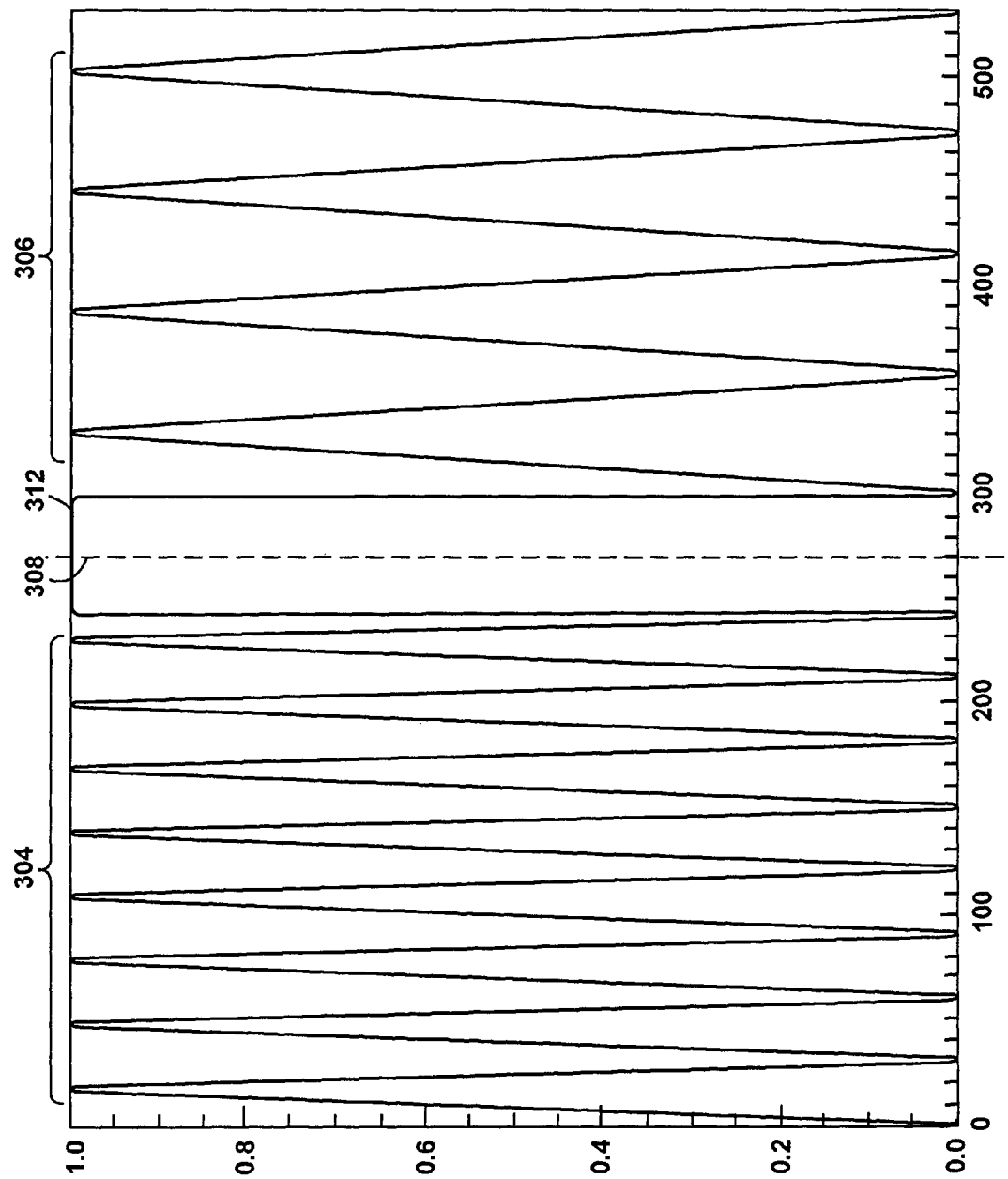
Figure 13:
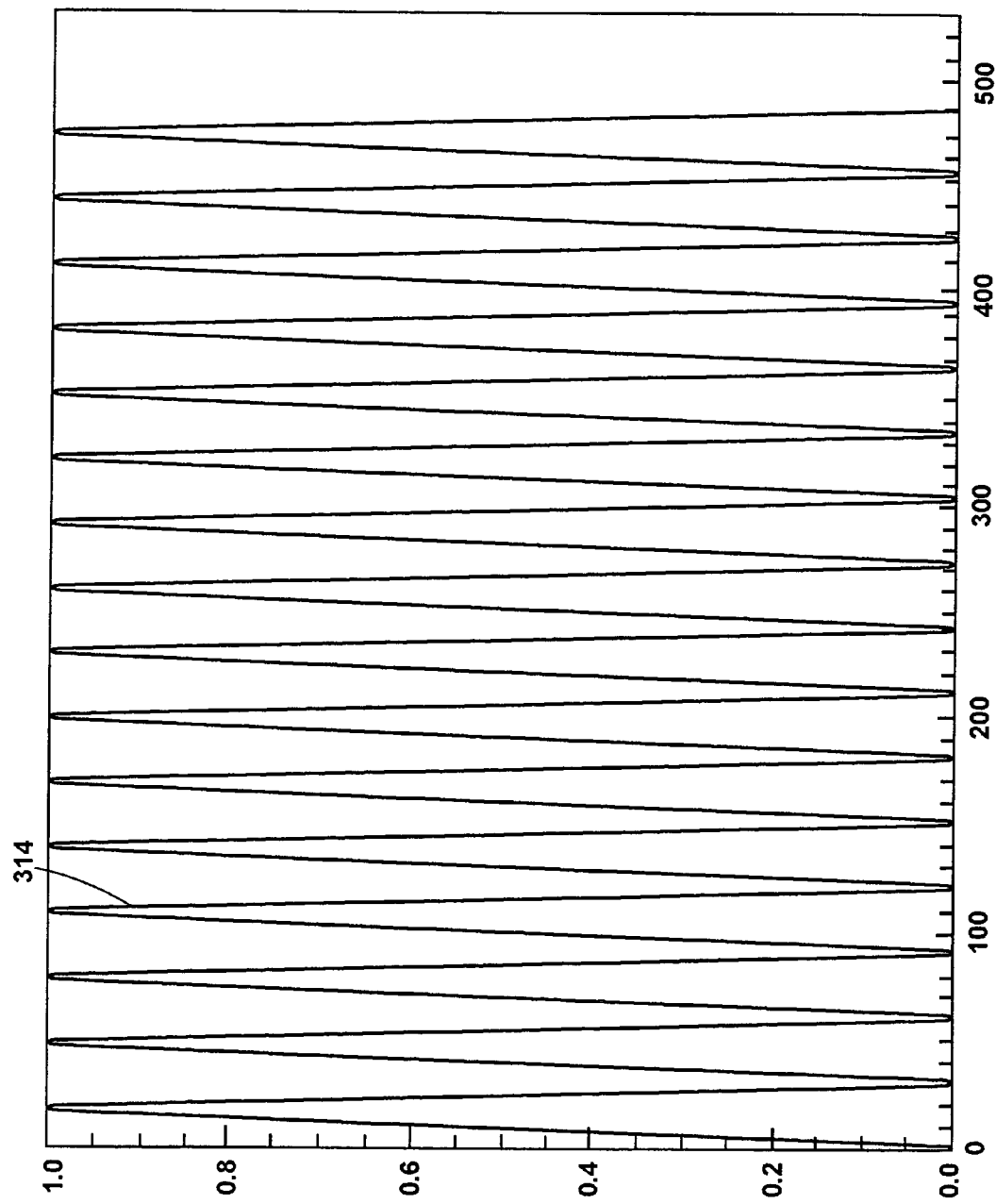

FIGS. 11, 12 and 13 show transparency patterns of alternative masks similar to that shown in FIG. 10. In FIG. 11, the pattern has a sine wave having a period similar to that of the sine function 304 of FIG. 10 and sine wave similar to that of the sine function 306 in FIG. 10, and has a completely opaque section 310 of the mask separating the two sine functions. In FIG. 12, the transparency pattern is similar to that shown in FIG. 10 except that a completely transparent section 312 of the mask separates the two sine functions.

In FIG. 13, the transparency pattern shows a single sine function 314 across the entire mask. In each of the transparency patterns shown in FIGS. 11, 12, and 13, it is possible to determine the location of the projected image reference line 132 corresponding to the mask reference line in the same manner as is done for the transparency pattern and shown in FIG. 10 and in the mask of FIG. 9. In addition, it is possible that the transparency pattern can be represented by other mathematical functions, such as a linear frequency chirp function, Chebyshev polynomials, Bessel function, and the like.

Figure 14:
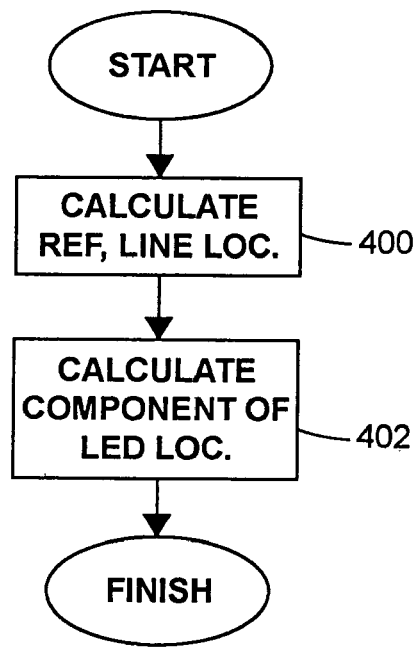
FIG. 14 is a flow diagram of the system and method of the present invention.

Turning now to FIG. 14 that shows a high level flow diagram of the method and system of the present invention. After initialization of the system, the beginning of the method starts with a block 400 that calculates the image reference line location for particular light source detected on an image detector. A block 402 then calculates the particular component of the location of that light source. It should be appreciated that even though no loop is shown in FIG. 14, the process as shown in FIG. 14 will be conducted over and over by the system to continuously track the LED's attached to an instrument in a surgical arena.

Figure 19:
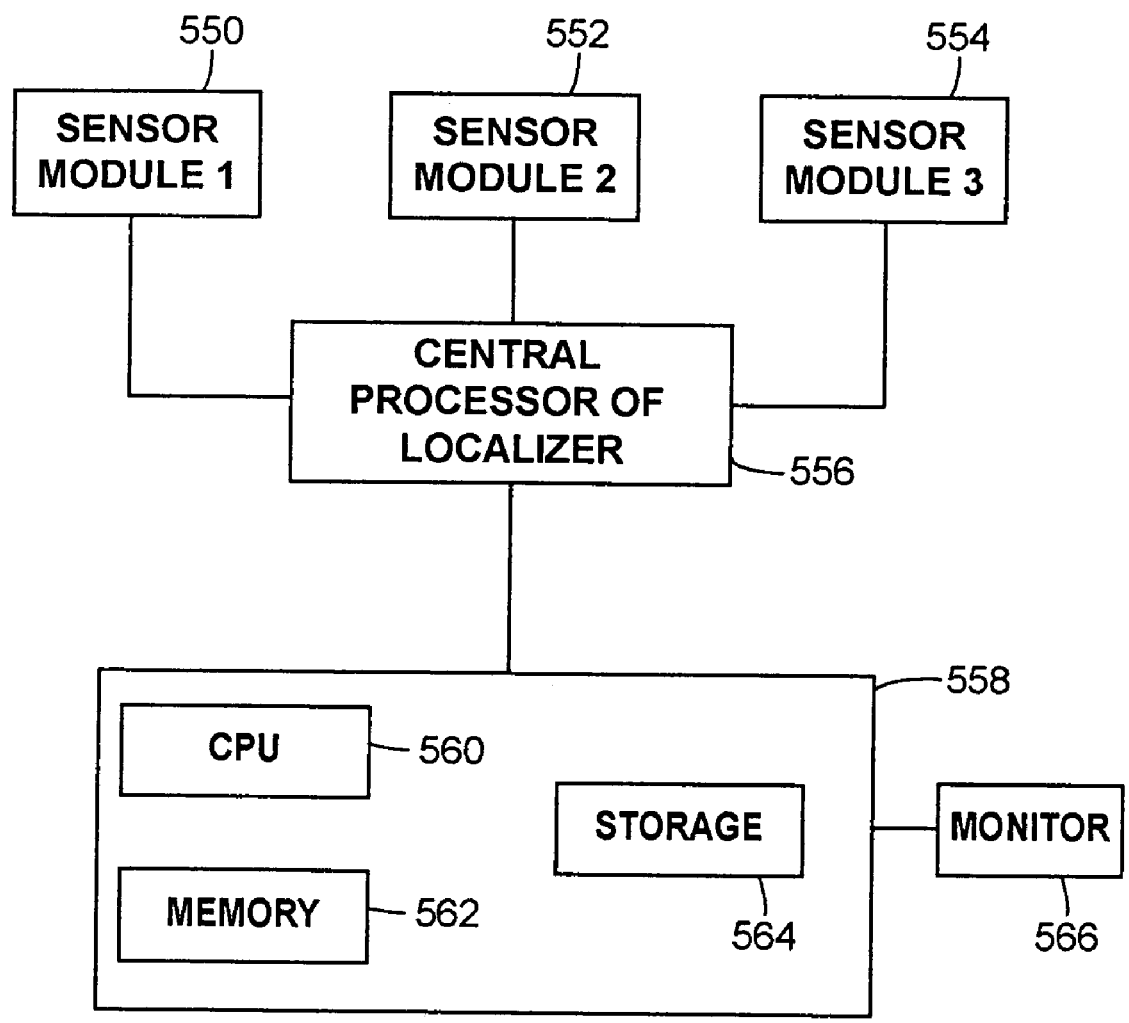
FIG. 19 is a schematic representation of a system combining multiple sensors of the present invention to determine a three dimensional location of a point source of light.

As shown in FIG. 19, a typical system will have three separate sensors CCD cameras 550, 552 and 554 each of which calculates a single component of the location of a particular light source. The calculation from the block 402 of one component of the location of the light source for each of the sensors 550, 552 and 554 is then passed to a localizing device 556 well known in the art, which then calculates the Cartesian coordinates of the light source and passes the coordinates of a particular LED to a personal computer 558 which contains an internal central processing unit 560, a memory 562 and a storage device 564. The personal computer 558 is also attached to a video monitor 566, which then displays the location of the tool based upon the location of each light source on a tool as determined by the localizer 556 based on data from sensors 550, 552 and 554. Here we assume that the light sources are individually and sequentially illuminated and that the locations of all light sources are tracked in parallel in order to determine the position of the whole tool.

Figure 15:
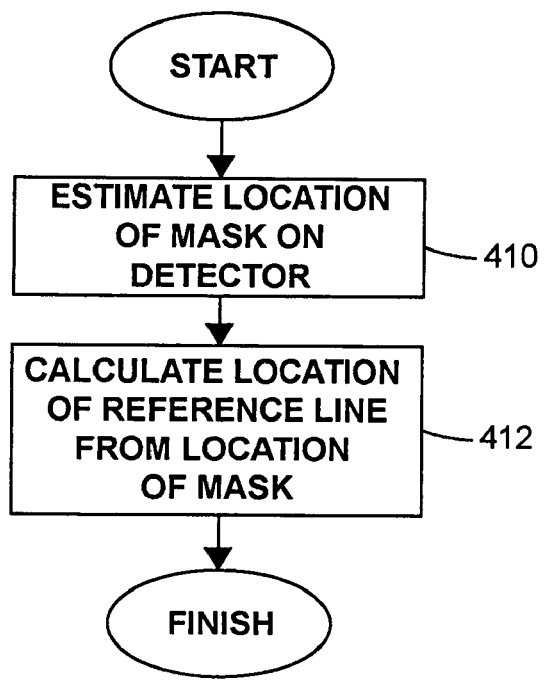
FIG. 15 is a flow diagram showing detail of the first block of FIG. 14.

In FIG. 15 there is a flow diagram for the calculation of the image reference line location generally identified by the block 400. A block 410 first estimates the location of the mask image on CCD. The estimation of the location of the mask image on CCD can be done by a wide variety of methods, including methods described with regard to FIG. 17 hereinafter as well as other methods based on the known configuration of the mask that is used for that particular detector unit. The estimate of the location of the mask image on CCD from the block 410 is then passed to a block 412 that calculates the actual location of the image reference line from the estimate made by the block 410. This calculated image reference line location is then passed to the block 402 in FIG. 14 for calculation of the component of the location of the radiation source.

Figure 16:
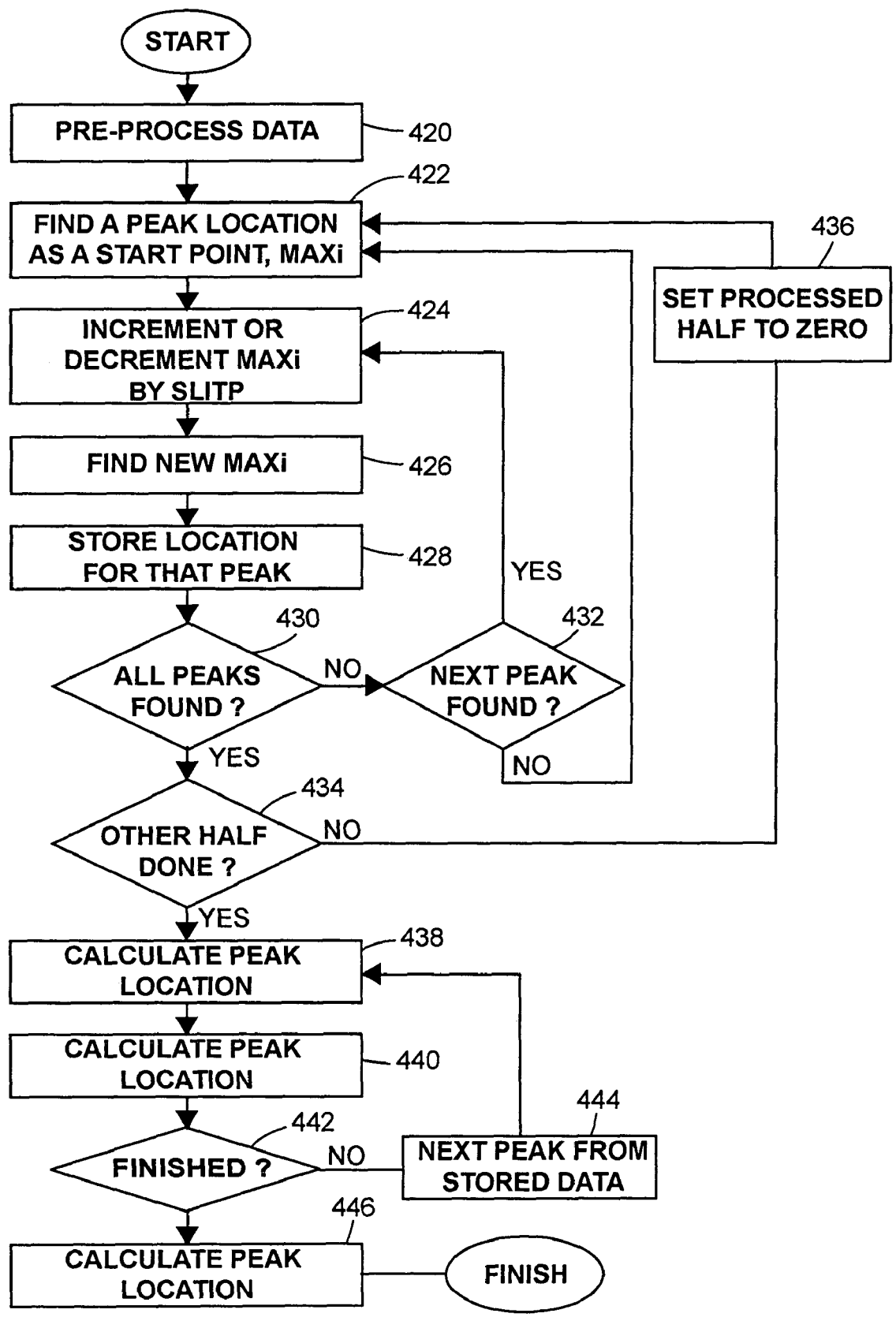
FIG. 16 is a flow diagram showing the detail of a further embodiment of the first block of FIG. 14.

FIG. 16 shows a more detailed flow diagram of one embodiment of a method and system to calculate the image reference line location as shown of the block 400 in FIG. 14. Control first passes to an optional block 420 that preprocesses the data to smooth the data and remove bias from the data in a manner as described in FIG. 17 or a similar method. The resulting data will look similar to FIG. 24. Control then passes to a block 422 that finds the maximum value, or the highest peak, of either the pre-processed data or the raw data. The block 422 stores the CCD index of this maximum value as $Max_i$ and the block 422 also calculates and stores a stop threshold value (SV) as a fraction of the maximum value, such as $SV=0.1*Max_i$. The initial value for $Max_i$ and the stop threshold value are stored in memory of the calculating unit 106. At this point control then passes to a block 424 and increments the initial value of $Max_i$ by the slit parameter, which is the average distance in pixels between adjacent slits. The slit parameter will be a known parameter for each particular mask used in the system and method of the present invention. For purpose of description of this embodiment, the slit parameter is set to 31, the number of pixels between adjacent slits. After the block 424 increments $Max_i$ by the slit parameter to give $Max_i$ est then a block 426 determines the maximum intensity for the pixel corresponding to the incremented $Max_{i\ est}$ and the nearby pixels on either side of $Max_{i\ est}$ and replaces $Max_{i\ est}$ with the location of the maximal nearby pixel and resets $Max_i$ to the location of this pixel. The value of $Max_i$ for that particular peak is then stored in the memory 562 by a block 428. After the block 428 stores the data for the $Max_i$ for the particular peak, a block 430 then determines if all peaks on that side of the original start point $Max_i$ have been found. This is done by comparing the number of peaks found with the number of slits on that half of the mask or by other known methodology. If all of the peaks on that half of the image have not been found, a block 432 searches for the next peak. If a next peak is found, that is a peak having a value greater than the SV, control branches by the yes branch back to the block 424 which again increments the value of the recently stored $Max_i$ by the slit parameter and the process in the blocks 426, 428 and 430 is repeated until such time as the block 432 search indicates that there are no additional peaks, that is there are no more peaks with an intensity greater than SV. Control passes back to the block 422 that sets $Max_i$ to the initial value for $Max_i$ that has been stored in the memory of the calculating unit 106. The block 424 then decrements the initial value of $Max_i$ by the slit parameter and the process of the blocks 426, 428, 430, and 432 are repeated until the block 430 determines that all peaks on one half of the mask image have been found. At that time control then passes to a block 434 that determines if the values for $Max_i$ for the other half of the mask 102 have been determined. If the values for $Max_i$ for the other half of the mask 102 have not been determined control passes to a block 436, which sets all the data of the mask image within the range of the half of the mask image that has its peaks found to zero and the process loops back to the block 422 which finds the highest peak of the remaining data and sets $Max_i$ to the CCD index value for that peak. The process then repeats the process of the blocks 424, 426 and 428, 430, and 432 until each peak on that side of the mask 102 has been identified. At that time control then passes again to the block 434, which determines that all peaks have been determined. This method determines the actual location for each particular peak within the mask image.

In the block 422 of FIG. 16, we used the highest peak as the start point to find all the peaks. Although it is one of the most reliable ways to choose the start point, other alternate methods can also work. For example, one can start from the two outermost peaks. To do so, one first finds the maximum value of the data. Then one sets one third of the maximum value as a threshold. One then starts from CCD index 0 and increments the index until one finds a pixel its value is larger than the threshold. From this pixel, one uses the next 31 (slit parameter) pixels and finds the index of the pixel that maximum value among these 31 pixels. This pixel is the location of left outer most peak. Using the same process outlined above, the location of the right most peak is determined. From the knowledge of these two start points, the process outlined in the blocks 424, 426, 428, 430, 432, and 434 can be used to find all other peaks.

Control then passes to a block 438, which calculates the location of each actual peak that has been identified with a $Max_i$ above. The actual location of each peak is then recorded by a block 440 into an array after which a block 442 determines whether or not each peak has been calculated and recorded. If there are further peaks to be calculated, a block 444 chooses the next peak from the previously stored data and passes control back to the block 438 that calculates the location of the new peak, followed by the block 440 storing the data and the block 442 determining whether all peaks have been calculated. After all peaks have been calculated control then passes to a block 446, which calculates the actual location of the image reference line. This can be done by a variety of mathematical methods including taking the mean of the locations of all stored peaks.

Figure 17:
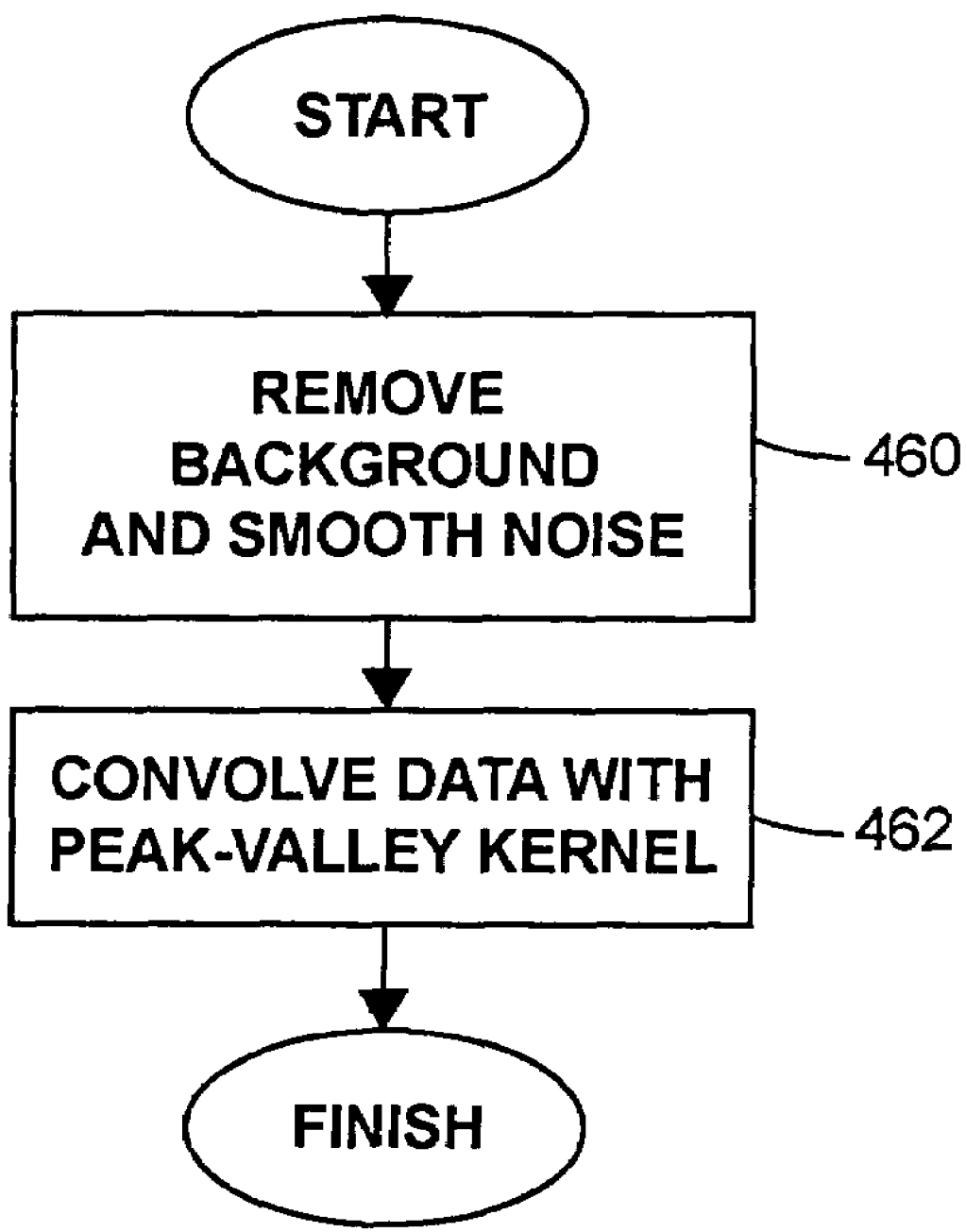
FIG. 17 is a flow diagram showing the detail of a still further embodiment of the first block of FIG. 14.

Turning now to FIG. 17, a flow diagram is shown for one method to pre-process the CCD data before determining the initial value of $Max_i$. In FIG. 17, data such as shown in FIG. 22 is filtered by a block 460 to improve the signal to noise ratio by removing background scatter and noise from the data shown in FIG. 22. Methods to remove this background scatter and noise can be any of the conventional filtering routines commonly used to remove data scatter and background noise including the use of various filters such as boxcar filters, etc. The data that results from the block 460 filtering the data will look like the data in FIG. 23. It should be noted that the data in FIG. 23 is much better behaved and is more regular than the data in FIG. 22 however the data in FIG. 23 still has a noticeable bias among the peaks of about 300 units. This is because of diffraction created through the slits in the mask 102. To remove this bias, the data from FIG. 23 and the block 460 is then convolved using a kernel in pixels equal to the distance between the centers of adjacent slits. As noted above, the value of the kernel is the same as the slit parameter in the presently described embodiment. A block 462 convolves the data from FIG. 23 with the value of the kernel, in this embodiment, 31. Other methods, such as second-order derivatives of data of FIG. 23, or multiplication of data of FIG. 23 with the second-order derivatives of data of FIG. 23, can be also used to remove the bias. Alternatively, one can use data of FIG. 23 to find all the peaks and not perform the bias removal step.

Figure 20:
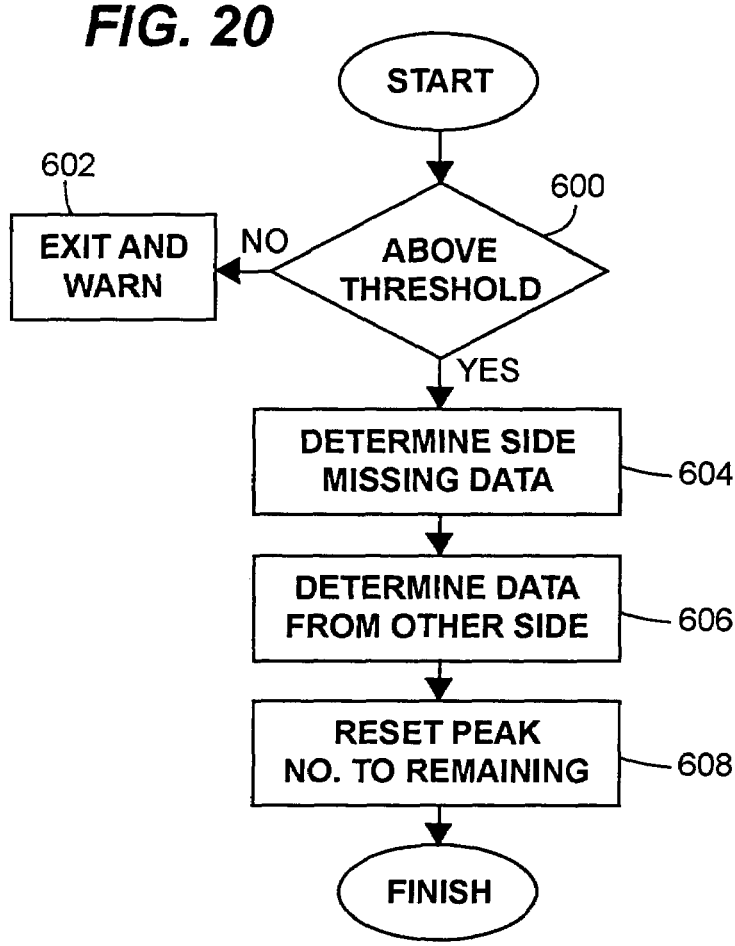
FIG. 20 is a flow diagram of a method to determine if a position can be determined where less than all of the peaks are visible to the detector.
Figure 21:
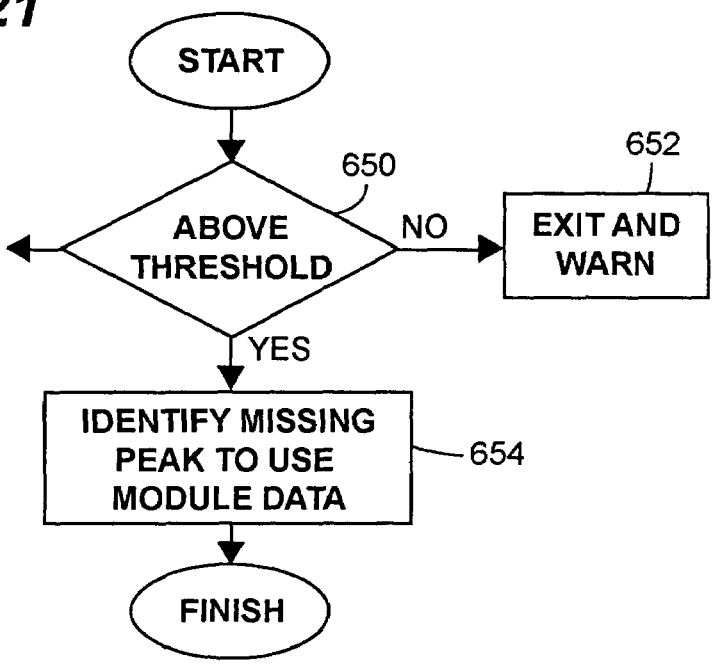
FIG. 21 is a further embodiment of a method to determine if a position can be determined where less than all peaks are visible to the detector.
Figure 25:
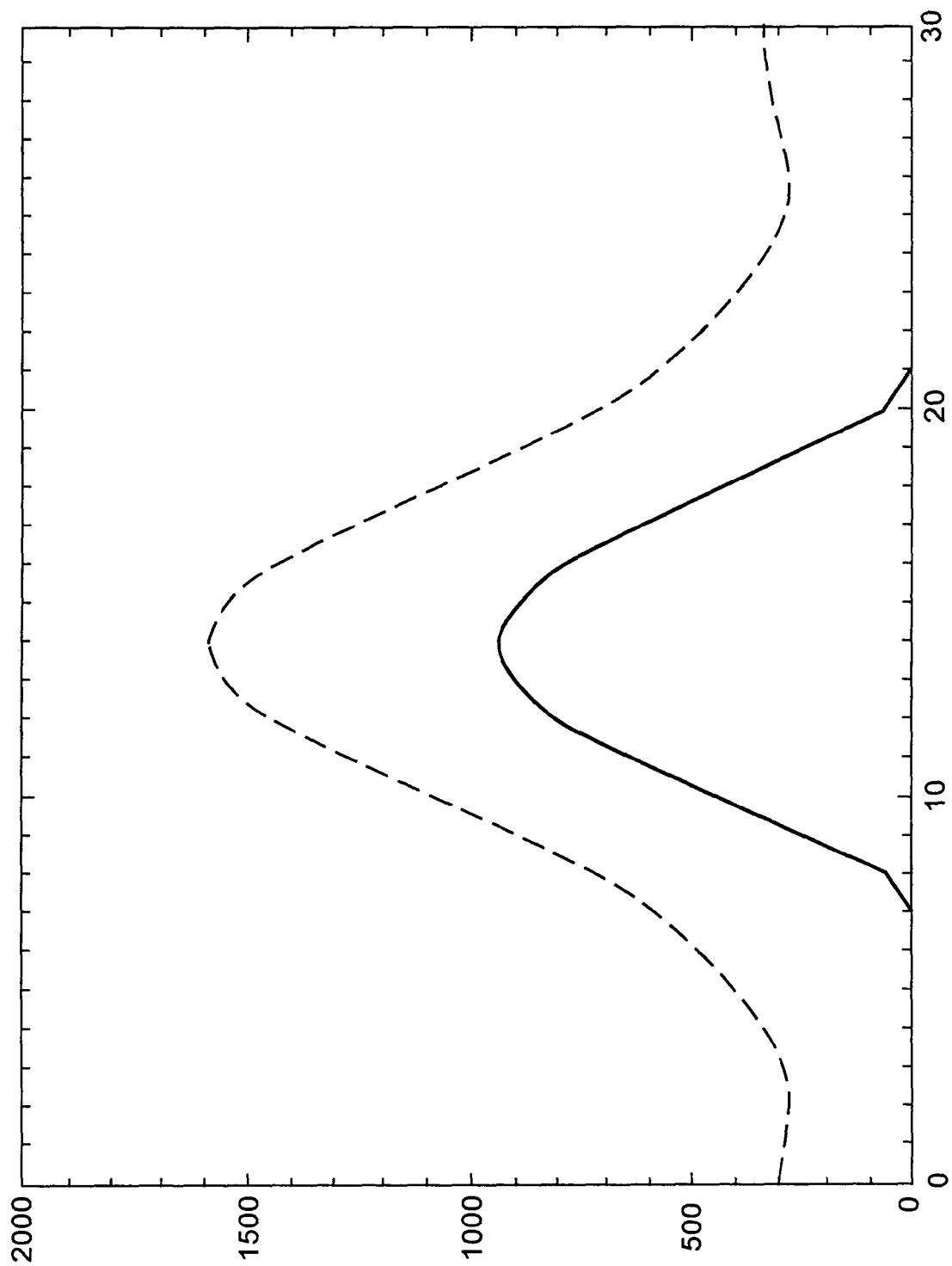
FIG. 25 is a plot of one peak of smoothed data from FIG. 23 and of that same peak data after the threshold value has been subtracted.

With reference to FIGS. 20 and 21, two alternative methods for determining whether or not the mask image data can be used to calculate the position of a component of a light source are shown. Prior to beginning the process as shown in FIG. 16, the system will perform an initialization process. As part of this process, the system will find the highest peak in the mask image and set a threshold value to some percentage of that value, typically 30%. FIG. 25 shows the data of FIG. 23 for the tenth peak as the dashed line and shows the truncated data after applying the threshold value and setting the negative values to zero as a solid line. The system will then look for the number of peaks that exceed this threshold value and compare that number to the expected number of peaks. If the count of the number of peaks conducted by the system is less than the expected number of peaks, the system will pass control to a block 600, which determines whether or not the total number of identified peaks is greater than or equal to a predetermined minimum peak number threshold value. This system will have determined a minimum peak number threshold value that indicates a minimum number of peaks that must be present such that the location of the image reference line can be calculated with sufficient accuracy for safe use. For instance, in the data such as shown in FIG. 22 based on the mask of FIG. 2, there are thirty peaks, it may be determined that five peaks can be missing and there will still be sufficient data that can be used as described below to calculate a position of the image reference line with sufficient precision. It should be noted for the method shown in FIG. 20 that if the threshold value is 25 peaks, the actual data that will be used to calculate the image reference line will only use 20 peaks as discussed later. In this regard, if the threshold value is exceeded, control passes to a block 604 that determines from which side of the center line the data is missing. Since the mask will be constructed in such a way that there will be a substantial amount of the image detector surface 120 that will not be used to determine the location of the radiation source in any given situation if the image is partially off the surface to either the left or the right, it will be a simple matter for the system to determine that the data to right side of the image is blank indicating that it is the left side of the image that has been displaced off the detector surface. Once the system knows whether it is the left side of the data or the right side of the data that is missing, the block 606 then deletes the same number of peaks from the side of the data not missing so as to balance the data around the potential or estimated image reference line. A block 608 then sets this new number to the value for x. In the example that being used, if 5 peaks are missing from the left end of the mask image data then the corresponding 5 peaks on the right end of the data are deleted leaving a total of 20 peaks. In this case, the block 608 sets x to 20, the number of usable peaks and in the process as shown in FIG. 16, the process will begin with the block 420.

In FIG. 21 an alternative method of determining whether or not the system can use less than all the data and a method of compensating for the missing data. Initially a block 650 determines whether or not the number of peaks available is higher or equal to a predefined minimum number of peak threshold value. If the value is lower than the predefined threshold value then a block 652 sends a warning alarm that displays a warning to the user on the monitor 566. An audible alarm may also be used. If the number is higher than the threshold value then control passes to a block 654 that then identifies those missing peaks in a manner similar to that described relative to the block 604. The difference is that the block 654 will use a mathematic model that represents the pattern on the mask with the length unit set to 1. Because the location of all imaged peaks is calculated in the model, the first step is to use the detected peak locations and the model to calculate a scale factor and an offset. Then the scale factor and the offset are used to match the model to the detected peak locations. Finally, any missing peak locations are replaced with the model peak location. After this, we can calculate the image reference line location as the mean of all peak locations. The advantage of this more elaborate method is that no peak locations are deleted. Therefore the statistical reliability of the calculated image reference line location is greater. Another alternative method to fill in the missing peak locations is to mathematically fit the detected peak locations to their corresponding data in the model. It is then possible to use the fitting parameters and the model to fill in the missing peak locations. Since the mask reference line 154 is a known location on the mathematical model, if the above data fitting method is used, the location of the image reference line 132 can be calculated directly from the data fitting parameters.

Figure 18:
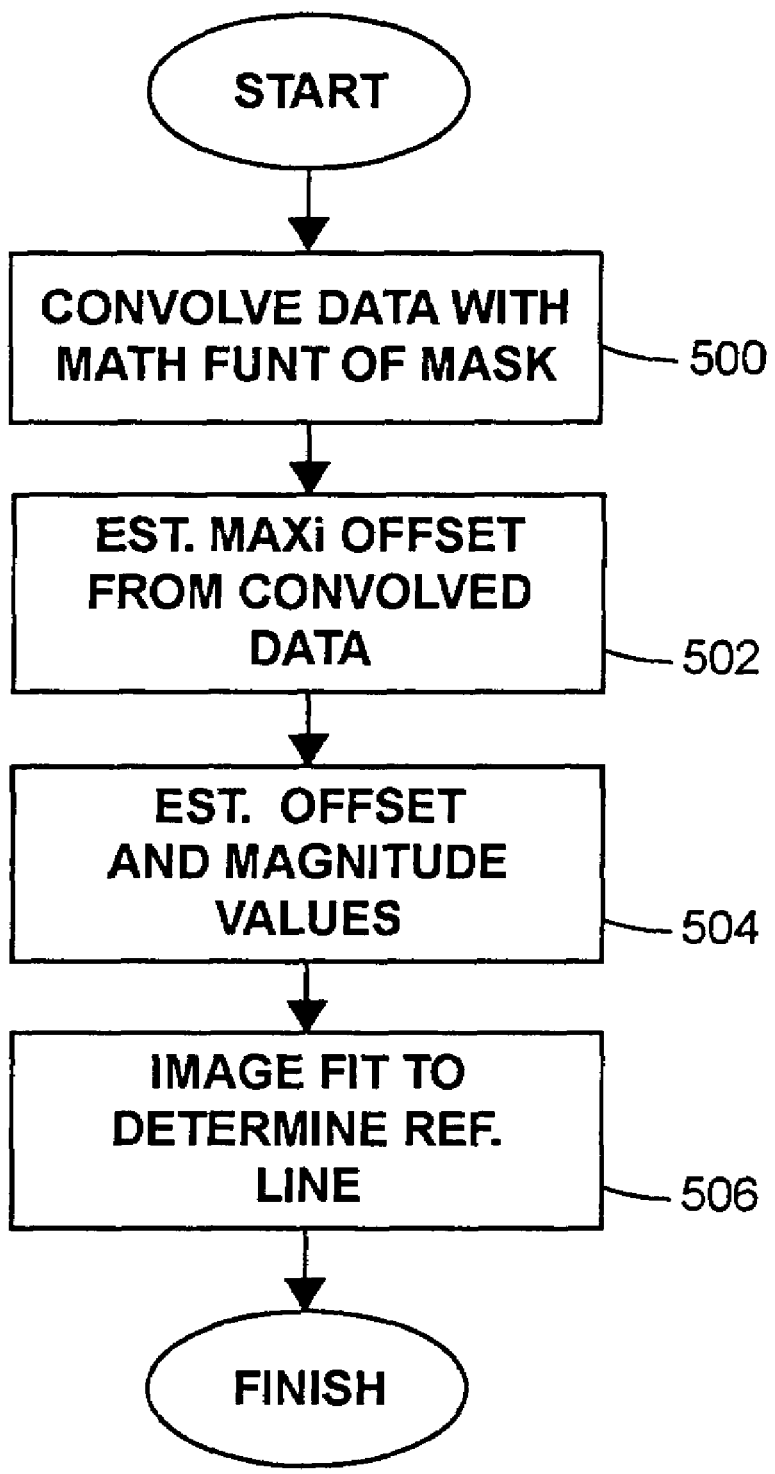
FIG. 18 is a flow diagram of an alternative method of the present invention.

An alternative method of determining the location of the image reference line is shown in FIG. 18. This method is particularly usable with masks that have variable transparencies based on a mathematical function such as shown in FIG. 9–13. This method also could be used with the other masks as described above, since these masks are also defined by a mathematical function. In this case, a block 500 convolves the data received in the image detector 104 from the mask 102 such as data shown in FIG. 26 with the formula that represents the mathematical description of the mask 102. The convolved data will take the form as shown in FIG. 27. A block 502 estimates the initial $Max_i$ value from the convolved data as shown in FIG. 27 as the data point with the maximum value. A block 504 then estimates the value of the image reference line offset, $Offset_{RL}$ and the magnitude of the $Max_i$ peak, $I_{Max}$. For the mask 302, the $Offset_{RL}$ is estimated as $Max_i-T$, where T is the base period in the mathematical formula describing the transparency of the mask 302. For some masks, such as the mask shown in FIG. 13, there will be no offset and $Offset_{RL}=Max_i$. The $I_{Max}$ is then used to estimate the Amplitude, Amp, of the function using a starting estimate of 95% of the image maximum or $I_{Max}*0.95$. A block 506 fits the data as shown in FIG. 26 to the following function using the estimates of the $Offset_{RL}$ and $I_{Max}$ that were determined by the block 504 plus the value for the period of the function $T_1=30$.

$F(x)=Amp*0.5*(1+\sin(A1*(x-\text{offset})-\pi/2))$ for offset$-Lhf*T1<=x<=$offset $F(x)=Amp*0.5*(1+\sin(A2*(x-\text{offset})-\pi/2))$ for offset$<x<$offset$+Rhf*T1$ $F(x)=0$ elsewhere.

where Lhf, Rhf, A1, and A2 have the same values as in the function that defines the transparency on the mask 102, T1 is estimated as the base period value T, and Amp and $Offset_{RL}$ are the values estimated by the block 504.

Figure 26:
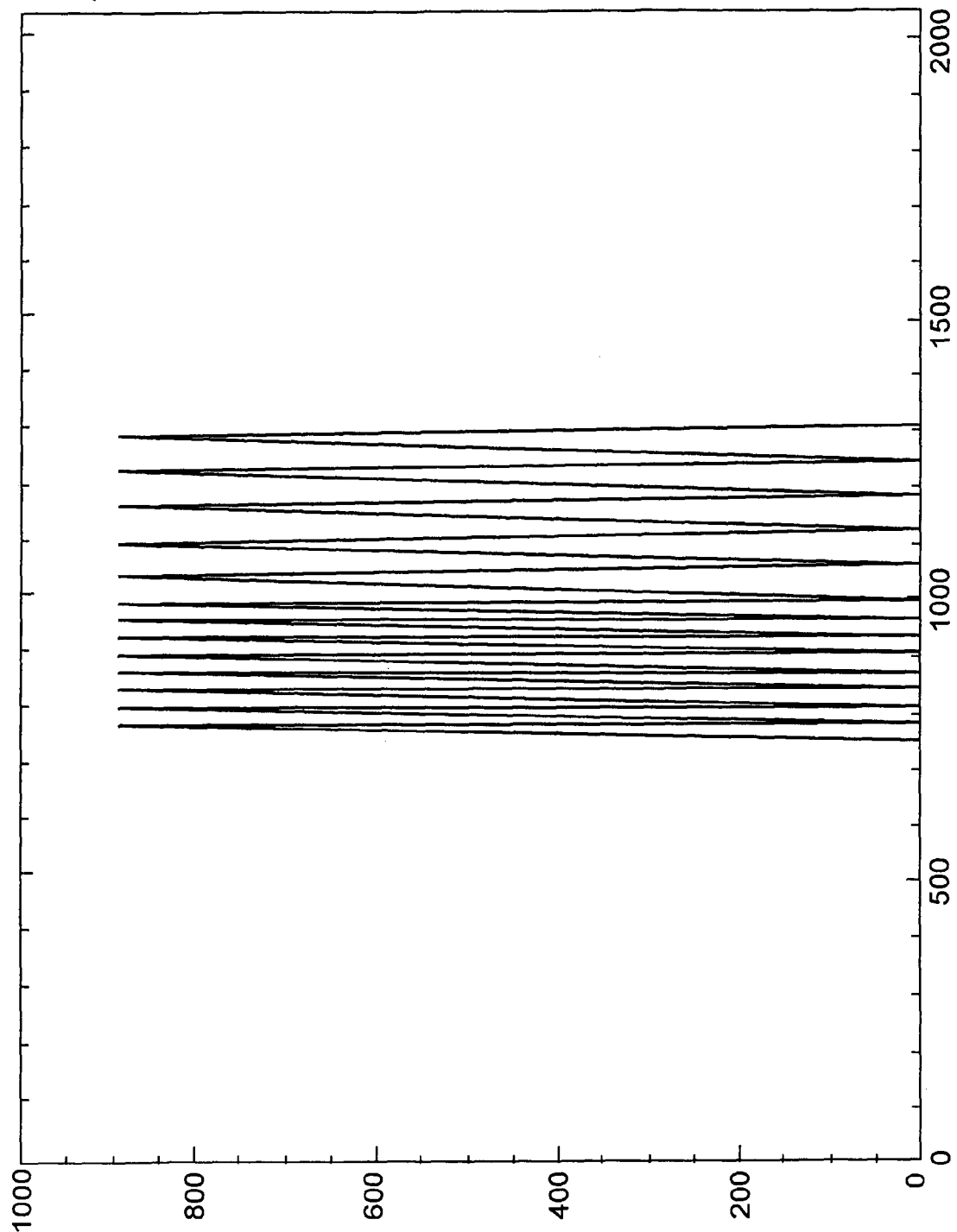
FIG. 26 is a plot of light intensity data on a detector passing through the mask of FIG. 9.
Figure 27:
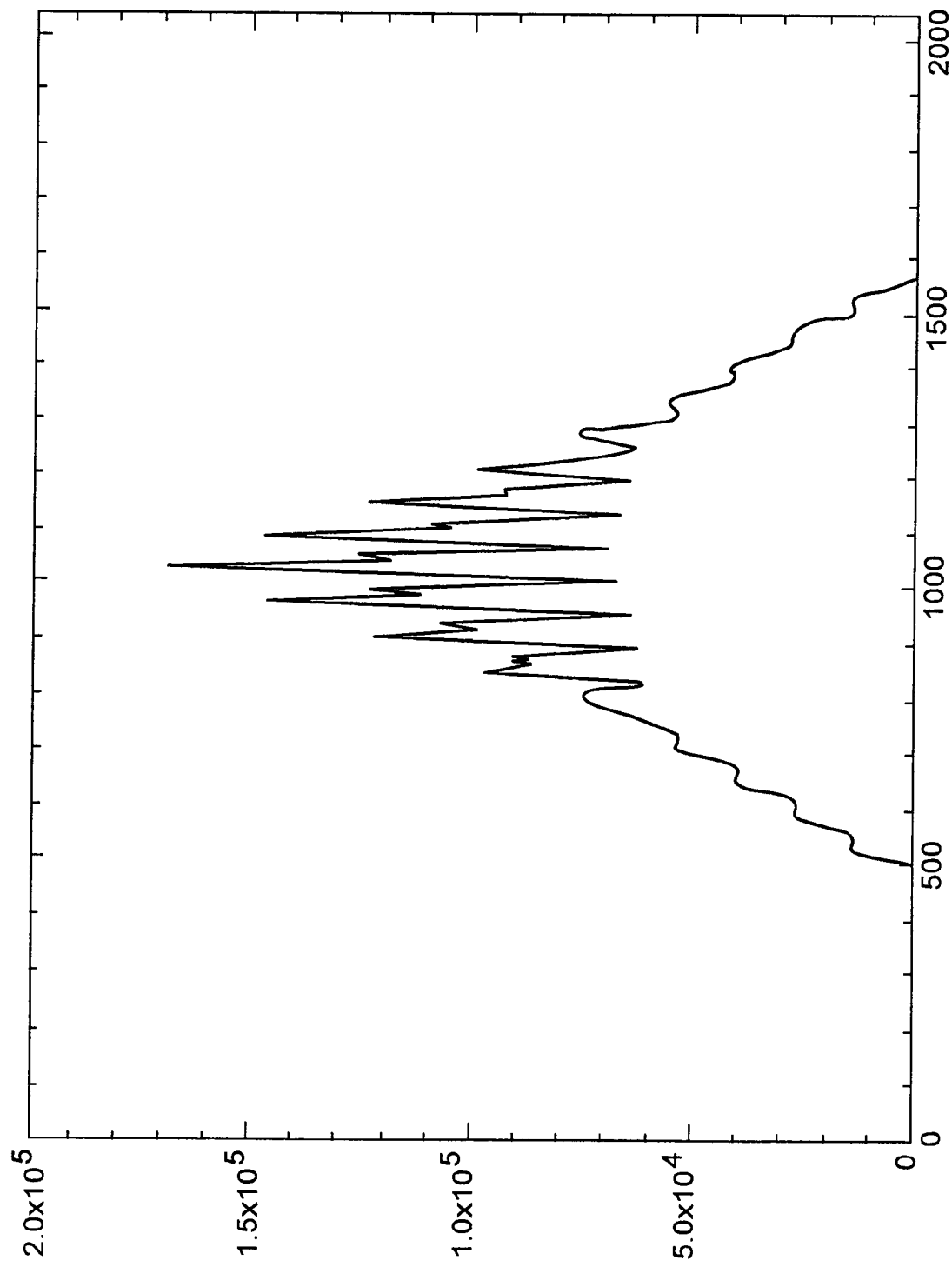
FIG. 27 is a plot of the data of FIG. 26 that has been convolved with the kernel of the pattern on the mask.

The above formula is then fit to the data of FIG. 26 using a nonlinear iterative data-fitting algorithm, such as Levenberg-Marquardt method or other similar mathematical methods, such as downhill simplex method, simulated annealing method, etc, to fit the mathematical function that defines the transparency of the mask 102 to the convolved image data to a predetermined error level, such as less than 0.2% change in subsequent iterations of the data fitting algorithm. The data fitting method shown in FIG. 18 provides a highly accurate value for the location of the image reference line, which then can be used by the block 412 of FIG. 15 to determine the component of the location of the radiation source.

Figure 28:
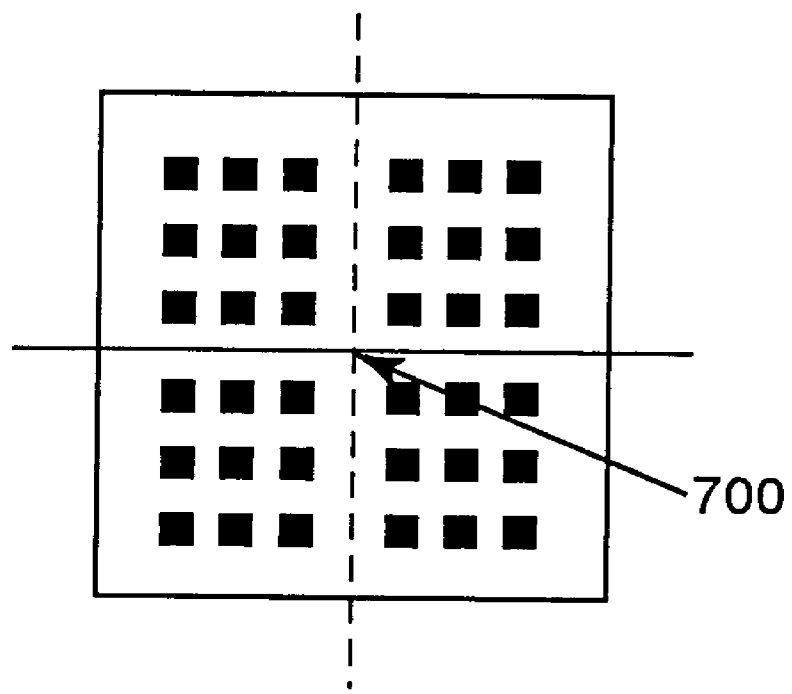
FIG. 28 is a plan view of a still further alternative mask pattern design.
Figure 29:
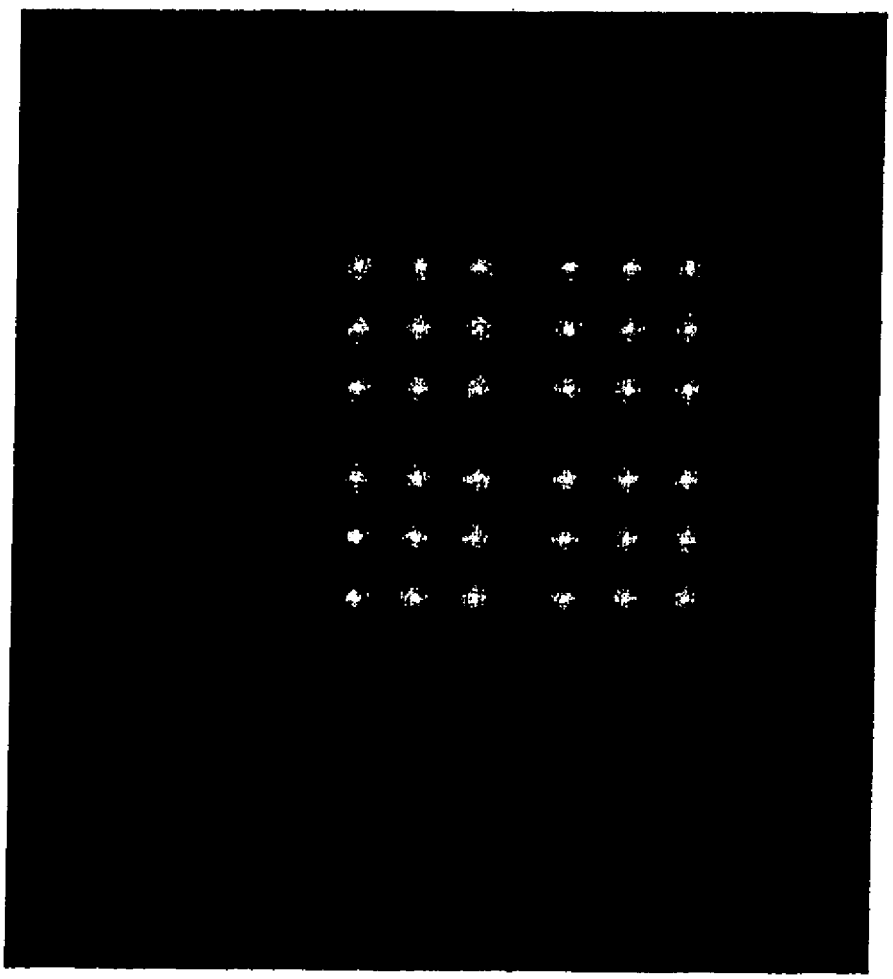
FIG. 29 is a view of an image created on a detector from the mask of FIG. 28.

The above description and discussion has been primarily directed toward one dimensional (1D) image detectors and the methods to process the image to find the location of the image reference line within the image. The same method can be easily extended to two dimensional (2D) mask imaged by two dimensional image detectors, such as CCD used in digital photo cameras or digital video camera. Some example of 2D CCDs are Kodak KAF-4202, a 2048×2048 pixels CCD; Sony ICX285 1392×1040 pixels CCD. To use a mask similar to FIG. 2 of a 1D system, a 2D mask of FIG. 28 that contains 36 transparent squares in an opaque mask can be used. This mask has two mask reference lines that are perpendicular to each other and intersect at a center point or reference point 700 on the 2D mask. A mask image of this 2D mask on the 2D CCD image detector will look like the image shown in FIG. 29. Once the mask image of the 2D mask is obtained, one can use method similar to the methods outlined in above FIGS. 15, 16, 17, 20, and 21 to first calculate the exact locations of all detected peaks and then calculate the location of the image reference point as the center of the 36 peaks.

It is also possible to use a variable transparency mask on a 2D mask. In this case, a 2D mask can be designed that follows a 2D mathematic function, such as a 2D sin function. It is possible to use the method similar to the 1D method outlined in FIG. 18 to iteratively fit the 2D image data to the 2D mathematic function and then find the location of the image reference point once the data fitting is done.

As noted previously, for a localizer that is made of 1D detectors, there must be at least three sensors to determine the coordinates of the location of the radiation source. This is because the 1D sensors are angular or planar cameras that each determine an angle θ, that is, they can only determine the plane that the radiation source is located on. It takes at least three planes to determine an intersection point of the planes. However, for localizer that is made of 2D detectors, only two are needed to determine the location of the radiation source, because 2D camera with the reference point on the mask defines a line in the 3D space, and two lines will determine a unique intersection point.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of determining a component of a location of a radiation source within a three dimensional volume, the method comprising the steps of:
    passing radiation from the radiation source through a mask having a series of openings onto a detector surface, wherein the series of openings has a predetermined mathematical relationship among the openings within the series of openings and wherein the series of openings define a mask reference line, to create a mask image having a series of peaks, and having an image reference line within the mask image that can be located and wherein at least 50% of the mask image is projected onto the detector surface;
    calculating a location of the mask image on the detector surface;
    calculating a location of the image reference line within the mask image; and
    calculating the component of the location of the radiation source from the calculated location of the image reference line within the mask image.

2. The method of claim 1 wherein the location of the mask image on the detector surface is calculated using substantially all of the mask image.

3. The method of claim 1 wherein the predetermined mathematical relationship among the openings is a series of equally spaced slits on either side of a central opaque section wider than the spacing between adjacent slits.

4. The method of claim 1 wherein the predetermined mathematical relationship among the openings is a series of equally spaced slits on either side of a central opaque section narrower than the spacing between adjacent slits.

5. The method of claim 1 wherein the predetermined mathematical relationship among the openings is a series of equally spaced slits on either side of a central slit that is wider than the other slits.

6. The method of claim 1 wherein the predetermined mathematical relationship among the openings is a series of equally spaced slits on either side of a central slit that is narrower than the other slits.

7. The method of claim 1 wherein there are two or more series of slits.

8. The method of claim 1 wherein the predetermined mathematical relationship among the openings is a transparency pattern variable in the direction parallel to the longitudinal direction of the detector surface and is constant in the direction perpendicular to the longitudinal direction of the detector surface.

9. The method of claim 8 wherein the transparency pattern is a mathematical function.

10. The method of claim 9 wherein the mathematical function is a sine function.

11. The method of claim 10 wherein the sine function has a different period on either side of the mask reference line.

12. The method of claim 1 wherein the calculating of the location of the image reference line includes the steps of:
    identifying a characteristic of the image reference line; and
    locating a portion of the image that corresponds to the characteristic of the image reference line.

13. The method of claim 12 that includes the step of compensating in the calculation for missing or invalid peaks.

14. The method of claim 1 wherein the calculation of the location of the image reference line includes the steps of:
    locating each peak of the image first on a first portion of the mask image and second on a second portion of the mask image; and
    calculating the location of the image reference line from the location of each valid peak in the image.

15. The method of claim 1 wherein the calculation of the location of the image reference line includes the step of convolving of the image with a kernel based on the predetermined mathematical relationship among the openings.

16. The method of claim 15 wherein the calculation of the location of the image reference line includes the step of fitting the image to a function based on the predetermined mathematical relationship among the openings using an iterative data fitting algorithm.

17. The method of claim 1 wherein the calculation of the location of the image reference line includes the step of filtering the image to minimize background noise.

18. The method of claim 1 wherein the calculation of the location of the image reference line includes the step of estimating an estimated location of the image reference line within the mask image; and calculating an actual location of the image reference line within the mask image from the estimated location of the image reference line within the mask image.

19. The method of claim 1 that includes the step of reporting if the image is at either extreme of the image detector.

20. The method of claim 1 wherein the mask reference line is not offset from a middle of the mask.

21. The method of claim 1 wherein the mask reference line is offset from a middle of the mask by a predetermined value.

22. The method of claim 1 wherein the image detector is a charge coupled device one pixel wide and a length longer than a width of the series of slits in the mask.

23. The method of claim 22 wherein the light emitting diode emits infrared radiation.

24. The method of claim 1 wherein the source of radiation is a light emitting diode.

25. The method of claim 1 wherein the mask creates a second image reference line perpendicular to the image reference line and wherein the image reference line and the second image reference line intersect to form an image reference point.

26. A system for determining a component of a location of a radiation source within a three dimensional volume comprising:
    a mask having a series of openings wherein the series of openings has a predetermined mathematical relationship among the openings within the series of openings, wherein the series of openings define a mask reference line;
    a detector surface spaced from the mask wherein the mask creates a mask image on the detector surface having a series of peaks and having an image reference line within the mask image that can be located and wherein at least 50% of the mask image is projected onto the detector surface;

a first circuit to calculate a location of the image reference line within the mask image; and a second circuit to calculate the component of the location of the radiation source from the calculated location of the image reference line within the mask image.

27. The system of claim 26 wherein the location of the mask image on the detector surface is calculated using substantially all of the mask image.

28. The system of claim 26 wherein the predetermined mathematical relationship among the openings is a series of equally spaced slits on either side of a central opaque section wider than the spacing between adjacent slits.

29. The system of claim 26 wherein the predetermined mathematical relationship among the openings is a series of equally spaced slits on either side of a central opaque section narrower than the spacing between adjacent slits.

30. The system of claim 26 wherein the predetermined mathematical relationship among the openings is a series of equally spaced slits on either side of a central slit that is wider than the other slits.

31. The system of claim 26 wherein the predetermined mathematical relationship among the openings is a series of equally spaced slits on either side of a central slit that is narrower than the other slits.

32. The system of claim 26 wherein there are two or more series of slits.

33. The system of claim 26 wherein the predetermined mathematical relationship among the openings is a transparency pattern variable in the direction parallel to the longitudinal direction of the detector surface and is constant in the direction perpendicular to the direction of the detector surface.

34. The system of claim 33 wherein the transparency pattern is a mathematical function.

35. The system of claim 34 wherein the mathematical relationship is a sine function.

36. The system of claim 35 wherein the sine function has a different period on either side of the mask reference line.

37. The system of claim 26 wherein the first circuit includes a third circuit to estimate of the location of the image reference line by identifying a characteristic of the image reference line of the mask; and locating a portion of the image that corresponds to the characteristic of the image reference line.

38. The system of claim 26 wherein the first circuit locates each peak of the image first on a first portion of the mask image and second on a second portion of the mask image; and calculates the location of the image reference line from the location of each valid peak in the mask image.

39. The system of claim 38 that includes a fourth circuit to compensate in the calculation for missing or invalid peaks.

40. The system of claim 26 wherein the first circuit also convolves of the mask image with a kernel based on the predetermined mathematical relationship among the openings.

41. The system of claim 40 wherein the first circuit fits the mask image to a function based on the predetermined mathematical relationship among the openings using an iterative data fitting algorithm.

42. The system of claim 26 wherein the first circuit also filters the mask image to minimize background noise.

43. The system of claim 26 wherein the first circuit also estimates an estimated location of the image reference line within the mask image; and calculates an actual location of the image reference line within the mask image from the estimated location of the image reference line within the mask image.

44. The system of claim 26 that includes a fifth circuit to report if the image is at either extreme of the image detector.

45. The system of claim 26 wherein the mask reference line is not offset from a middle of the mask.

46. The system of claim 26 wherein the mask reference line is offset from a middle of the mask by a predetermined value.

47. The system of claim 26 wherein the image detector is a charge coupled device one pixel wide and has a length longer than a width of the series of slits in the mask.

48. The system of claim 26 wherein the source of radiation is a light emitting diode.

49. The system of claim 48 wherein the light emitting diode emits infrared radiation.

50. The system of claim 26 wherein the mask creates a second image reference line perpendicular to the image reference line and wherein the image reference line and the second image reference line intersect to form an image reference point.

51. A sensor for determining a component of a location of a radiation source within a three dimensional volume comprising:

a mask having a series of openings wherein the series of openings has a predetermined mathematical relationship among the openings within the series of openings and wherein the series of opening defines a mask reference line;

a detector surface spaced from the mask wherein the series of openings in the mask creates a mask image on the detector surface having a series of peaks and an image reference line within the mask image that can be located and wherein at least 50% of the mask image is projected onto the detection surface; and a calculating unit to determine a location of the image reference line within the mask image and the component of the location of the radiation source from the calculated location of the image reference line within the mask image.

52. The sensor of claim 51 wherein the calculating unit calculates the location of the mask reference line on the detector surface using substantially all of the mask image.

53. The sensor of claim 51 wherein the fixed relationship of the openings is a series of equally spaced slits on either side of a central opaque section wider than the spacing between adjacent slits.

54. The sensor of claim 51 wherein the fixed relationship of the openings is a series of equally spaced slits on either side of a central opaque section narrower than the spacing between adjacent slits.

55. The sensor of claim 51 wherein the fixed relationship of the openings is a series of equally spaced slits on either side of a central slit that is wider than the other slits.

56. The sensor of claim 51 wherein the fixed relationship of the openings is a series of equally spaced slits on either side of a central slit that is narrower than the other slits.

57. The sensor of claim 51 wherein there are two or more series of slits.

58. The sensor of claim 51 wherein the fixed relationship of the openings is a transparency pattern variable in the direction parallel to the longitudinal direction of the detector surface and is constant in a direction perpendicular to the longitudinal direction of the detector surface.

59. The sensor of claim 58 wherein the transparency pattern is a mathematical function.

60. The sensor of claim 59 wherein the mathematical function is a sine function.

61. The sensor of claim 60 wherein the sine function has a different period on either side of the mask reference line.

62. The sensor of claim 51 wherein the mask reference line is not offset from a middle of the mask.

63. The sensor of claim 51 wherein the mask reference line is offset from a middle of the mask by a predetermined value.

64. The sensor of claim 51 wherein the image detector is a charge coupled device one pixel wide and has a length longer than a width of the series of slits in the mask.

65. The sensor of claim 51 wherein the image detector detects infrared radiation.

66. The sensor of claim 51 wherein the mask creates a second image reference line perpendicular to the image reference line and wherein the image reference line and the second image reference line intersect to form an image reference point.

* * * * *